US012052971B2

(12) United States Patent
Susin Arrieta et al.

(10) Patent No.: US 12,052,971 B2
(45) Date of Patent: Aug. 6, 2024

(54) SOLANACEOUS PLANT CAPABLE OF STENOSPERMOCARPIC FRUIT FORMATION

(71) Applicant: Nunhems B.V., Nunhem (NL)

(72) Inventors: Ignacio Susin Arrieta, Paterna (ES); Gowtham Prakash, Nunhem (NL); Maria Rocio Aparicio Cirre, Paterna (ES); Wim Vriezen, Nunhem (NL); Lieke Mertens, Nunhem (NL); Louis Gisberts, Nunhem (NL); Inka Gawenda, Magdeburg (DE); Nelson Davila Olivas, Nunhem (NL); Carlos Hernando Galeano Mendoza, Davis, CA (US)

(73) Assignee: NUNHEMS B.V., Nunhem (NL)

( * ) Notice: Subject to any disclaimer, the term of this patent is extended or adjusted under 35 U.S.C. 154(b) by 111 days.

(21) Appl. No.: 17/413,448

(22) PCT Filed: Dec. 4, 2019

(86) PCT No.: PCT/EP2019/083605
§ 371 (c)(1),
(2) Date: Jun. 11, 2021

(87) PCT Pub. No.: WO2020/120242
PCT Pub. Date: Jun. 18, 2020

(65) Prior Publication Data

US 2022/0053731 A1 Feb. 24, 2022

(30) Foreign Application Priority Data

Dec. 13, 2018 (EP) .................................... 18212422

(51) Int. Cl.
*A01H 6/82* (2018.01)
*A01H 5/08* (2018.01)
*A01H 5/10* (2018.01)

(52) U.S. Cl.
CPC ............... *A01H 6/825* (2018.05); *A01H 5/08* (2013.01); *A01H 5/10* (2013.01)

(58) Field of Classification Search
None
See application file for complete search history.

(56) References Cited

FOREIGN PATENT DOCUMENTS

| | | | |
|---|---|---|---|
| CN | 107254478 | A | 10/2017 |
| WO | 99/21411 | A1 | 5/1999 |
| WO | 2008/152134 | A1 | 12/2008 |
| WO | 2012/087140 | A2 | 6/2012 |
| WO | 2013/078319 | A1 | 5/2013 |
| WO | 2016/120438 | A1 | 8/2016 |
| WO | 2017/125931 | A1 | 7/2017 |

OTHER PUBLICATIONS

Schrick et al, 2014, BMC Biology, 12:1-20.*
Hanania et al, 2007, Transgenic Res, 16:515-525.*
"SubName: Full=Homeobox-leucine zipper protein ROC5 {ECO:0000313:EMBL:PHT87216.1}", Database UniProt [Online], retrieved from EBI accession No. UniProt:A0AIU8FZU7, Database accession No. A0AIU8FZU7, XP002789675, May 10, 2017, 2 pages.*
"Homeobox-leucine zipper protein ROC5 isoform XI [Solanum lycopersicum]", Database NCBI [Online], Database accession No. XP 004234441, XP002789678, Aug. 8, 2018, 2 pages.
"SubName: Full=Homeobox-leucine zipper protein ROC5 {ECO:0000313:EMBL:PHT53105.1}", Database UniProt [Online], retrieved from EBI accession No. UniProt:A0A2G2X6G6, Database accession No. A0A2G2X6G6, XP002789677, Jan. 31, 2018, 2 pages.
"SubName: Full=Homeobox-leucine zipper protein ROC5 {ECO:0000313:EMBL:PHU23006.1}", Database UniProt [Online], retrieved from EBI accession No. UniProt:A0A2G3CWC3, Database accession No. A0A2G3CWC3, XP002789676, Jan. 31, 2018, 2 pages.
Acciarri, et al., "Genetically modified parthenocarpic eggplants: improved fruit productivity under both greenhouse and open field cultivation", BMC Biotechnology, Vo. 2, Issue 1, Apr. 4, 2002, pp. 1-7.
Akbudak, et al., "In vitro and in vivo behavior of gamma-irradiated tomato (*Lycopersicon esculentum*) pollen", New Zealand Journal of Crop and Horticultural Science, 2009, vol. 37, issue 4, 2009, pp. 361-367.
Allen, et al., "Transcript-specific, single-nucleotide polymorphism discovery and linkage analysis in hexaploid bread wheat (*Triticum aestivum* L.)", Plant biotechnology journal, vol. 9, Issue 9, Dec. 1, 2011, pp. 1086-1099.
Antonio Tiezzi, "The pollen tube cytoskeleton", Electron Microscopy Reviews, vol. 4, Issue 2, 1991, pp. 205-219.
Comai, et al., "Efficient discovery of DNA polymorphisms in natural populations by Ecotilling", vol. 37. Issue 5, Mar. 2004, pp. 778-786.
European Search Report for EP Patent Application No. 18212422.2, Issued on Apr. 12, 2019, 4 pages.
Fang, et al., "Getting Started in Gene Orthology and Functional Analysis", PLoS Computational Biology, vol. 6, Issue 3, Mar. 26, 2010, p. e1000703.

(Continued)

*Primary Examiner* — Jason Deveau Rosen
(74) *Attorney, Agent, or Firm* — Arentfox Schiff LLP

(57) ABSTRACT

The present invention relates to a plant of the family Solanaceae comprising in its genome at least one copy of a mutant allele which causes stenospermocarpic fruit formation when present in homozygous form. The present invention further relates to pollen and seed produced by the plant of the present invention, seed from which the plant of the present invention can be grown and a part from the plant according to the present invention. The present invention further relates to a method of identifying and/or selecting a plant according to the present invention and a method of producing a plant according to the present invention. The present invention further relates to the use of the plant of the present invention as a crop for consumption or as a source of propagation material. The present invention further relates to the use of a nucleic acid for the identification of a plant of the present invention or for breeding plants of the present invention.

21 Claims, 3 Drawing Sheets

Specification includes a Sequence Listing.

(56) References Cited

OTHER PUBLICATIONS

Hanania, et al., "Silencing of chaperonin 21, that was differentially expressed in inflorescence of seedless and seeded grapes, promoted seed abortion in tobacco and tomato fruits", Transgenic Research, vol. 16, Issue 4, Aug. 2007, pp. 515-525.

Henikoff et al., "Tilling. Traditional mutagenesis meets functional genomics", Plant Physiology, vol. 135, Issue 2, Jun. 2004, pp. 630-636.

Henikoff, et al., "Amino acid substitution matrices from protein blocks", Proceedings of the National Academy of Sciences of the United States of America, vol. 89, Issue 22, Nov. 15, 1992, pp. 10915-10919.

International Search Report for PCT Patent Application No. PCT/EP2019/083605, Issued on Jan. 22, 2020, 5 pages.

Morita, et al., "Molecular characterization of mutations induced by gamma irradiation in rice", Genes & genetic systems, vol. 84, Issue 5, 2009, pp. 361-370.

Ng, et al., "SIFT: predicting amino acid changes that affect protein function", Nucleic Acids Research, vol. 31, Issue 13, Jul. 1, 2003, pp. 3812-3814.

Olimpieri, et al., "Constitutive co-suppression of the GA 20-oxidase1 gene in tomato leads to severe defects in vegetative and reproductive development", Plant Science, vol. 180, Issue 3, Mar. 2011, pp. 496-503.

Rotino, et al., "Open field trial of genetically modified parthenocarpic tomato: seedlessness and fruit quality", BMC Biotechnology, vol. 5, Issue 1, Dec. 21, 2005, pp. 1-8.

Ruan, et al., "Molecular regulation of seed and fruit set", Trends in Plant Science, vol. 17, Issue 11, Nov. 2012, pp. 656-665.

Till, et al., "A protocol for Tilling and Ecotilling in plants and animals", Nature protocols, Dec. 29, 2006, vol. 1, Issue 5, pp. 2465-2477.

Till, et al., "Discovery of chemically induced mutations in rice by Tilling", BMC Plant Bbiology, vol. 7, Issue 1, Apr. 11, 2007, pp. 1-12.

Till, et al., "Discovery of induced point mutations in maize genes by Tilling", BMC Plant Biology, Vo. 4, Issue 1, Jul. 28, 2004, pp. 1-8.

Till, et al., "High-throughput Tilling for *Arabidopsis*", *Arabidopsis* Protocols, 2006, pp. 127-135.

Yin, et al., "The Defl-I9-iaaM-containing construct efficiently induces parthenocarpy in cucumber", Cellular & Molecular Biology Letters, vol. 11, Issue 2, Jun. 1, 2006, pp. 279-290.

* cited by examiner

Figure 2

SEQUENCE LISTING

```
<160> NUMBER OF SEQ ID NOS: 14

<210> SEQ ID NO 1
<211> LENGTH: 815
<212> TYPE: PRT
<213> ORGANISM: Capsicum annuum

<400> SEQUENCE: 1

Met Ser Phe Gly Gly Phe Ile Gly Ser Ser Ser Gly Gly Gly Gly Gly
1               5                   10                  15

Ser Gly Val Ser Arg Leu Val Gly Asp Ser Pro Tyr Glu Ala Met Pro
            20                  25                  30

Thr Ala Thr Val Ala Gln Ser Gln Leu Ile Thr Ser Ser Leu Pro Gln
        35                  40                  45

Ser Ile Phe Asn Ser Ser Pro Leu Ser Leu Ala Leu Lys Pro Lys Met
    50                  55                  60

Glu Gly Ala Ser Asp Met Ser Leu Leu Ala Glu Asn Phe Gly Ala Val
65                  70                  75                  80
```

```
Ala Met Gly Arg Ser Asp Glu Asn Asp Ser Arg Ser Pro Ser Asp His
                85                  90                  95

Leu Asp Gly Gly Gly Ser Gly Asp Asp Met Glu Ala His Val Gly Ser
            100                 105                 110

Ser Ser Arg Lys Lys Lys Tyr His Arg His Thr Pro Tyr Gln Ile Gln
        115                 120                 125

Glu Leu Glu Ala Cys Phe Lys Glu Asn Pro His Pro Asp Glu Lys Ala
    130                 135                 140

Arg Leu Glu Leu Gly Lys Arg Leu Ser Leu Glu Thr Arg Gln Val Lys
145                 150                 155                 160

Phe Trp Phe Gln Asn Arg Arg Thr Gln Met Lys Thr Gln Leu Glu Arg
                165                 170                 175

His Glu Asn Ser Met Leu Lys Gln Glu Asn Asp Lys Leu Arg Leu Glu
            180                 185                 190

Asn Met Ala Met Lys Glu Ala Met Arg Gly Pro Thr Cys His Gln Cys
        195                 200                 205

Gly Gly Gln Ala Ile Leu Gly Glu Ile His Met Glu Glu His His Leu
    210                 215                 220

Lys Ile Glu Asn Ala Arg Leu Arg Asp Glu Tyr Asn Arg Ile Cys Leu
225                 230                 235                 240

Met Ala Asn Lys Val Leu Gly Arg Pro Leu Ser Ser Phe Pro Ser Pro
                245                 250                 255

Met Pro Ala Gly Met Gly Asn Phe Gly Leu Glu Leu Ala Val Gly Arg
            260                 265                 270

Asn Gly Phe Gly Ala Met Asn Ser Val Asp Ala Ala Leu Pro Met Gly
        275                 280                 285

Leu Asp Phe Gly Asn Gly Ile Ser Ser Ala Thr Ile Pro Val Ile Ser
    290                 295                 300

Pro Arg Pro Ile Pro Asn Met Thr Gly Ile Asp Val Ser Phe Asp Lys
305                 310                 315                 320

Thr Val Leu Met Glu Leu Ala Phe Ala Ala Met Asn Glu Leu Val Lys
                325                 330                 335

Leu Ala Glu Ile Ser Gly Pro Leu Trp Phe Arg Ser Leu Asp Gly Asn
            340                 345                 350

Gly Glu Glu Leu Asn Leu Glu Glu Tyr Ala Arg Ser Phe Pro Pro Cys
        355                 360                 365

Ile Gly Met Lys Pro Ala Asn Phe Thr Ala Glu Ala Thr Lys Ala Thr
    370                 375                 380

Gly Thr Val Met Ile Asn Ser Leu Ala Leu Val Glu Thr Leu Met Asp
385                 390                 395                 400

Thr Ser Gln Trp Val Asp Thr Phe Ser Ser Ile Val Gly Arg Thr Ser
                405                 410                 415

Ser Met Asn Leu Ile Ser Ser Ser Ser Gly Gly Gly Arg Asn Gly Asn
            420                 425                 430

Leu Gln Leu Ile Gln Ala Glu Phe Gln Val Val Ser Ala Leu Val Pro
        435                 440                 445

Val Arg Gln Val Lys Phe Leu Arg Phe Cys Lys Gln His Ala Glu Gly
    450                 455                 460

Val Trp Ala Val Val Asp Val Ser Val Asp Ala Ile Gln Glu Gly Ser
465                 470                 475                 480

Gln Pro Arg Glu Ala Gly Asn Cys Arg Arg Leu Pro Ser Gly Cys Ile
                485                 490                 495
```

```
Val Gln Asp Leu Ser Asn Gly Tyr Ser Lys Val Ile Trp Ile Glu His
            500                 505                 510

Met Glu Tyr Asp Glu Ser Thr Ile His Asn Tyr Tyr Arg Ala Phe Ile
        515                 520                 525

Lys Ser Gly Leu Gly Phe Gly Ala Gln Arg Trp Ile Ala Ala Leu Gln
    530                 535                 540

Arg Gln Cys Glu Cys Leu Ala Ile Ile Met Ser Ser Thr Val Ser Ser
545                 550                 555                 560

Gly Asp Asn Ala Val Val Gly Pro Ser Gly Arg Arg Ser Ile Ala Met
                565                 570                 575

Leu Ala Arg Arg Val Thr Cys Asn Phe Cys Ala Gly Val Cys Gly Thr
            580                 585                 590

Phe Tyr Lys Trp Glu Pro Ile Gln Ser Gly Ser Gly Glu Glu Thr Lys
        595                 600                 605

Leu Met Met Arg Lys Ser Val Gly Glu Leu Gly Glu Pro Ser Gly Val
    610                 615                 620

Met Leu Ser Ala Thr Arg Thr Ile Trp Leu Pro Ile Thr His Gln Arg
625                 630                 635                 640

Leu Phe Asp Phe Leu Arg Asn Ala Gln Thr Arg Arg Gln Trp Asp Val
                645                 650                 655

Leu Phe His Gly Asp Ala Met His Glu Ile Val His Ile Ala Lys Gly
            660                 665                 670

Gln Asp Leu Gly Asn Ser Ile Ser Leu Tyr Arg Thr Asn Val Thr Gly
        675                 680                 685

Ser Asp Gly Asn Gln Ser Ser Met Leu Tyr Leu Gln Asp Ser Cys Thr
    690                 695                 700

Asp Val Ser Gly Ser Ile Val Ser Tyr Ala Ala Val Asp Thr Ala Gln
705                 710                 715                 720

Met Asn Val Val Met Ser Gly Gly Asp Ser Ser Cys Val Thr Phe Leu
                725                 730                 735

Pro Ser Gly Phe Ala Ile Val Pro Asp Cys Phe Gly Asn Ser Asn Gly
            740                 745                 750

Val Thr Ser Asn Gly Met Leu Glu Lys Glu Asp Asn Gly Gly Arg Asn
        755                 760                 765

Asn Gly Ser Phe Leu Thr Val Gly Tyr Gln Ile Leu Val Asn Asn Leu
    770                 775                 780

Pro Gly Gly Asn Leu Thr Met Glu Ser Val Asn Thr Ile Asn Ser Phe
785                 790                 795                 800

Val Ser Arg Thr Leu Gly Gly Ile Lys Thr Ile Phe Gln Cys Asn
                805                 810                 815


<210> SEQ ID NO 2
<211> LENGTH: 2448
<212> TYPE: DNA
<213> ORGANISM: Capsicum annuum

<400> SEQUENCE: 2

atgagttttg gaggcttcat tggtagtagt agtggtggtg gtggtggttc tggggtttcg      60

agattggtgg gtgatagtcc atacgaagcc atgcctactg ctactgttgc tcagtcacaa     120

cttatcacat catctttacc tcagtctata tttaactctt ctccactatc tcttgctctt     180

aaaccgaaga tggaaggtgc aagtgacatg agtttgttag cggaaaattt tggtgctgtt     240

gcaatgggaa ggtcggatga gaacgatagc aggtccccta gtgaccactt agatggtggt     300

ggatcgggcg atgatatgga agctcacgtt ggtagctcat cgaggaagaa gaaataccat     360
```

```
aggcacactc cataccaaat tcaagaactt gaagcttgtt ttaaggagaa tccacaccct    420

gatgaaaaag ctagacttga acttggtaag aggttgtcgt tggaaaccag gcaggtgaag    480

ttttggtttc aaaataggag aactcagatg aagacccaat tggagcgcca tgaaaattca    540

atgttaaagc aagaaaatga caaactgcgc ctggagaaca tggcaatgaa ggaagctatg    600

agagggccaa cttgccacca atgtggtggc caagcaattc ttggagaaat acacatggaa    660

gagcatcatt tgaagattga gaatgctagg ctgagagatg aatacaatag gatctgtctt    720

atggcgaaca aggttttggg caggcctttg tcatctttcc ctagtccaat gccagctgga    780

atgggcaact ttggtttgga acttgctgtt ggaagaaacg gctttggtgc tatgaactct    840

gttgacgctg cattgccaat gggacttgat tttggtaatg gtatctcaag tgctactata    900

ccagtgattt cacctaggcc catccccaac atgactggta tagatgtatc ctttgataag    960

actgtgttaa tggagcttgc ttttgctgcc atgaatgagc tggttaagct ggctgagatc   1020

agtggtcctc tgtggtttag aagcttggat ggaaatgggg aagagttgaa ccttgaggag   1080

tatgctaggt cttttcctcc gtgtattggc atgaagcctg ccaacttcac agcagaagca   1140

acaaaggcaa ctggtacggt gatgatcaac agtctggcct tggtggagac tttaatggac   1200

acaagtcaat gggtggatac attctcaagc attgttggca gaacctcttc aatgaatttg   1260

atctccagca gctcgggtgg aggcaggaat ggcaatttgc aattgatcca agctgagttc   1320

caagttgtat ctgctttagt tcctgtccgt caagtaaaat ttctacgctt ctgcaagcaa   1380

catgctgaag gtgtctgggc agtggtggat gtgtctgttg atgcaatcca agagggttca   1440

caaccgcgtg aagctggaaa ctgcaggagg ctcccctcgg gatgtattgt gcaagacttg   1500

tccaatggat actcaaaggt tatttggatt gaacatatgg aatatgatga gagtaccatc   1560

cacaattact accgcgcttt catcaagtct ggcctgggct ttggtgccca acggtggatt   1620

gccgccctac aaaggcaatg tgagtgcttg gcaatcatca tgtcttctac tgtgtccagt   1680

ggggataacg cagttgttgg tcccagtggt cggagaagta ttgcaatgct ggctcgacgc   1740

gtgacttgca acttttgtgc tggggtttgt ggaacctttt acaagtggga accaatccaa   1800

tcagggagtg gagaggagac taagttgatg atgaggaaga gcgttggtga acttggtgag   1860

ccttctggtg tgatgttgag tgccaccagg accatctggc tgccgataac acatcaacgt   1920

ttgtttgact tcctgagaaa tgcacaaaca agaaggcaat gggatgtctt gttccatggt   1980

gatgccatgc acgaaatagt ccacattgcc aagggtcagg atcttggcaa tagcatctct   2040

ctctatcgta ctaatgtgac tggtagcgat ggtaatcaaa gtagtatgtt gtacttgcag   2100

gactcctgca ctgatgtgtc gggttcaatt gtatcatatg cagctgttga tactgcacaa   2160

atgaatgttg tgatgagtgg tggagattcc tcctgcgtga ctttcctgcc atctgggttt   2220

gccatagttc cagattgttt tgggaattcc aacggggtta ctagcaatgg aatgcttgaa   2280

aaagaggata atgggggtag gaacaatggg tctttcttga ctgtgggata tcaaatattg   2340

gtgaataact tgcctggagg aaatctcact atggaatcgg tcaacaccat taactctttc   2400

gtctcccgta ctctgggtgg tatcaaaact attttccagt gcaattaa                2448
```

<210> SEQ ID NO 3
<211> LENGTH: 181
<212> TYPE: PRT
<213> ORGANISM: Capsicum annuum

<400> SEQUENCE: 3

```
Met Ser Phe Gly Gly Phe Ile Gly Ser Ser Ser Gly Gly Gly Gly Gly
1               5                   10                  15

Ser Gly Val Ser Arg Leu Val Gly Asp Ser Pro Tyr Glu Ala Met Pro
            20                  25                  30

Thr Ala Thr Val Ala Gln Ser Gln Leu Ile Thr Ser Ser Leu Pro Gln
        35                  40                  45

Ser Ile Phe Asn Ser Ser Pro Leu Ser Leu Ala Leu Lys Pro Lys Met
    50                  55                  60

Glu Gly Ala Ser Asp Met Ser Leu Leu Ala Glu Asn Phe Gly Ala Val
65                  70                  75                  80

Ala Met Gly Arg Ser Asp Glu Asn Asp Ser Arg Ser Pro Ser Asp His
                85                  90                  95

Leu Asp Gly Gly Gly Ser Gly Asp Asp Met Glu Ala His Val Gly Ser
            100                 105                 110

Ser Ser Arg Lys Lys Lys Tyr His Arg His Thr Pro Tyr Gln Ile Gln
        115                 120                 125

Glu Leu Glu Ala Cys Phe Lys Glu Asn Pro His Pro Asp Glu Lys Ala
    130                 135                 140

Arg Leu Glu Leu Gly Lys Arg Leu Ser Leu Glu Thr Arg Gln Val Lys
145                 150                 155                 160

Phe Trp Phe Gln Asn Arg Arg Thr Gln Met Lys Thr Gln Leu Glu Arg
                165                 170                 175

Met Lys Ile Gln Phe
            180
```

<210> SEQ ID NO 4
<211> LENGTH: 546
<212> TYPE: DNA
<213> ORGANISM: Capsicum annuum

<400> SEQUENCE: 4

```
atgagttttg gaggcttcat tggtagtagt agtggtggtg gtggtggttc tggggtttcg     60

agattggtgg gtgatagtcc atacgaagcc atgcctactg ctactgttgc tcagtcacaa    120

cttatcacat catctttacc tcagtctata tttaactctt ctccactatc tcttgctctt    180

aaaccgaaga tggaaggtgc aagtgacatg agtttgttag cggaaaattt tggtgctgtt    240

gcaatgggaa ggtcggatga gaacgatagc aggtccccta gtgaccactt agatggtggt    300

ggatcgggcg atgatatgga agctcacgtt ggtagctcat cgaggaagaa gaaataccat    360

aggcacactc cataccaaat tcaagaactt gaagcttgtt ttaaggagaa tccacaccct    420

gatgaaaaag ctagacttga acttggtaag aggttgtcgt tggaaaccag gcaggtgaag    480

ttttggtttc aaaataggag aactcagatg aagacccaat tggagcgcat gaaaattcaa    540

ttttaa                                                               546
```

<210> SEQ ID NO 5
<211> LENGTH: 818
<212> TYPE: PRT
<213> ORGANISM: Capsicum chinense

<400> SEQUENCE: 5

```
Met Ser Phe Gly Gly Phe Ile Gly Ser Ser Ser Gly Gly Asp Gly Gly
1               5                   10                  15

Gly Gly Gly Ser Gly Val Ser Arg Leu Val Gly Asp Ser Pro Tyr Glu
            20                  25                  30

Ala Met Pro Thr Ala Thr Val Ala Gln Ser Gln Leu Ile Thr Ser Ser
```

```
        35                  40                  45

Leu Pro Gln Ser Ile Phe Asn Ser Ser Pro Leu Ser Leu Ala Leu Lys
    50                  55                  60

Pro Lys Met Glu Gly Ala Ser Asp Met Ser Leu Leu Ala Glu Asn Phe
65                  70                  75                  80

Gly Ala Val Ala Met Gly Arg Ser Asp Glu Asn Asp Ser Arg Ser Pro
                85                  90                  95

Ser Asp His Leu Asp Gly Gly Gly Ser Gly Asp Asp Met Glu Ala His
            100                 105                 110

Val Gly Ser Ser Ser Arg Lys Lys Lys Tyr His Arg His Thr Pro Tyr
        115                 120                 125

Gln Ile Gln Glu Leu Glu Ala Cys Phe Lys Glu Asn Pro His Pro Asp
    130                 135                 140

Glu Lys Ala Arg Leu Glu Leu Gly Lys Arg Leu Ser Leu Glu Thr Arg
145                 150                 155                 160

Gln Val Lys Phe Trp Phe Gln Asn Arg Arg Thr Gln Met Lys Thr Gln
                165                 170                 175

Leu Glu Arg His Glu Asn Ser Met Leu Lys Gln Glu Asn Asp Lys Leu
            180                 185                 190

Arg Leu Glu Asn Met Ala Met Lys Glu Ala Met Arg Gly Pro Thr Cys
        195                 200                 205

His Gln Cys Gly Gly Gln Ala Ile Leu Gly Glu Ile His Met Glu Glu
    210                 215                 220

His His Leu Lys Ile Glu Asn Ala Arg Leu Arg Asp Glu Tyr Asn Arg
225                 230                 235                 240

Ile Cys Leu Met Ala Asn Lys Val Leu Gly Arg Pro Leu Ser Ser Phe
                245                 250                 255

Pro Ser Pro Met Pro Ala Gly Met Gly Asn Phe Gly Leu Glu Leu Ala
            260                 265                 270

Val Gly Arg Asn Gly Phe Gly Ala Met Asn Ser Val Asp Ala Ala Leu
        275                 280                 285

Pro Met Gly Leu Asp Phe Gly Asn Gly Ile Ser Ser Ala Thr Ile Pro
    290                 295                 300

Val Ile Ser Pro Arg Pro Ile Pro Asn Met Thr Gly Ile Asp Val Ser
305                 310                 315                 320

Phe Asp Lys Thr Val Leu Met Glu Leu Ala Phe Ala Ala Met Asn Glu
                325                 330                 335

Leu Val Lys Leu Ala Glu Ile Ser Gly Pro Leu Trp Phe Arg Ser Leu
            340                 345                 350

Asp Gly Asn Gly Glu Glu Leu Asn Leu Glu Glu Tyr Ala Arg Ser Phe
        355                 360                 365

Pro Pro Cys Ile Gly Met Lys Pro Ala Asn Leu Thr Ser Glu Ala Thr
    370                 375                 380

Lys Ala Thr Gly Thr Val Met Ile Asn Ser Leu Ala Leu Val Glu Thr
385                 390                 395                 400

Leu Met Asp Thr Ser Gln Trp Val Asp Thr Phe Ser Ser Ile Val Gly
                405                 410                 415

Arg Thr Ser Ser Met Asn Leu Ile Ser Ser Ser Ser Gly Gly Ser Arg
            420                 425                 430

Asn Gly Asn Leu Gln Leu Ile Gln Ala Glu Phe Gln Val Val Ala Thr
        435                 440                 445

Leu Val Pro Val Arg Gln Val Lys Phe Leu Arg Phe Cys Lys Gln His
    450                 455                 460
```

```
Ala Glu Gly Val Trp Ala Val Val Asp Val Ser Val Asp Ala Ile Gln
465                 470                 475                 480

Glu Gly Ser Gln Pro Arg Glu Ala Gly Asn Cys Arg Arg Leu Pro Ser
                485                 490                 495

Gly Cys Ile Val Gln Asp Leu Ser Asn Gly Tyr Ser Lys Val Ile Trp
            500                 505                 510

Ile Glu His Met Glu Tyr Asp Glu Ser Thr Ile His Asn Tyr Tyr Arg
        515                 520                 525

Ala Phe Ile Lys Ser Gly Leu Gly Phe Gly Ala Gln Arg Trp Ile Ala
    530                 535                 540

Ala Leu Gln Arg Gln Cys Glu Cys Leu Ala Ile Ile Met Ser Ser Thr
545                 550                 555                 560

Val Ser Ser Gly Asp Asn Ala Val Val Gly Pro Ser Gly Arg Arg Ser
                565                 570                 575

Ile Ala Met Leu Ala Arg Arg Val Thr Cys Asn Phe Cys Gly Gly Val
            580                 585                 590

Cys Gly Thr Phe Tyr Lys Trp Glu Pro Ile Gln Ser Gly Ser Gly Glu
        595                 600                 605

Glu Thr Lys Leu Met Met Arg Lys Ser Val Gly Glu Leu Gly Glu Pro
    610                 615                 620

Ser Gly Val Met Leu Ser Ala Thr Arg Thr Ile Trp Leu Pro Ile Thr
625                 630                 635                 640

His Gln Arg Leu Phe Asp Phe Leu Arg Asn Ala Gln Thr Arg Arg Gln
                645                 650                 655

Trp Asp Val Leu Phe His Gly Asp Ala Met His Glu Ile Val His Ile
            660                 665                 670

Ala Lys Gly Gln Asp Leu Gly Asn Ser Ile Ser Leu Tyr Arg Thr Asn
        675                 680                 685

Val Thr Gly Ser Asp Gly Asn Gln Ser Ser Met Leu Tyr Leu Gln Asp
    690                 695                 700

Ser Cys Thr Asp Val Ser Gly Ser Ile Val Ser Tyr Ala Ala Val Asp
705                 710                 715                 720

Thr Ala Gln Met Asn Val Val Met Ser Gly Gly Asp Ser Ser Cys Val
                725                 730                 735

Thr Phe Leu Pro Ser Gly Phe Ala Ile Val Pro Asp Cys Phe Gly Asn
            740                 745                 750

Ser Asn Gly Val Thr Ser Asn Gly Met Leu Glu Lys Glu Asp Asn Gly
        755                 760                 765

Gly Arg Asn Lys Gly Ser Phe Leu Thr Val Gly Tyr Gln Ile Leu Val
    770                 775                 780

Asn Asn Leu Pro Gly Gly Asn Leu Thr Met Glu Ser Val Asn Thr Ile
785                 790                 795                 800

Asn Ser Phe Val Ser Arg Thr Leu Asp Gly Ile Lys Thr Ile Phe Arg
                805                 810                 815

Cys Asn

<210> SEQ ID NO 6
<211> LENGTH: 2457
<212> TYPE: DNA
<213> ORGANISM: Capsicum chinense

<400> SEQUENCE: 6

atgagttttg gaggcttcat tggtagtagt agtggtggtg acggtggtgg tggtggttct      60
```

```
ggggtttcga gattggtggg tgatagtcca tacgaagcca tgcctactgc tactgttgct    120

cagtcacaac ttatcacatc atctttacct cagtctatat ttaactcttc tccactatct    180

cttgctctta aaccgaagat ggaaggtgca agtgacatga gtttgttagc ggaaaatttt    240

ggtgctgttg caatgggaag gtcggatgag aacgatagca ggtcccctag tgaccactta    300

gatggtggtg gatcgggcga tgatatggaa gctcacgttg gtagctcatc gaggaagaag    360

aaataccata ggcacactcc ataccaaatt caagaacttg aagcttgttt taaggagaat    420

ccacaccctg atgaaaaagc tagacttgaa cttggtaaga ggttgtcgtt ggaaaccagg    480

caggtgaagt tttggtttca aaataggaga actcagatga agacccaatt ggagcgccat    540

gaaaattcaa tgttaaagca agaaaatgac aaactgcgcc tagagaacat ggcaatgaag    600

gaagctatga gagggccaac ttgccaccaa tgtggtggcc aagcaattct tggagaaata    660

cacatggaag agcatcattt gaagattgag aatgctaggc tgagagatga atacaatagg    720

atctgtctta tggcgaacaa ggttttgggc aggcctttgt catctttccc tagtccaatg    780

ccagctggaa tgggcaactt tggtttggaa cttgctgttg gaagaaacgg ctttggtgct    840

atgaactctg ttgacgctgc attgccaatg ggacttgatt ttggtaatgg tatctcaagt    900

gctactatac cagtgatttc acctaggccc atccccaaca tgactggtat agatgtatcc    960

tttgataaga ctgtgttaat ggagcttgct tttgctgcca tgaatgagct ggttaagctg   1020

gctgagatca gtggtcctct gtggtttaga agcttggatg gaaatgggga agagttgaac   1080

cttgaggagt atgctaggtc ttttcctccg tgtattggca tgaagcctgc caacttgaca   1140

tcagaagcaa caaaggcaac tggtacagtg atgatcaaca gtctggcctt ggtggagact   1200

ttaatggaca caagtcaatg ggtggataca ttctcaagca ttgttggcag aacctcttca   1260

atgaatttga tctccagcag ctcgggtgga agcaggaatg gcaatttgca attgatccaa   1320

gctgagttcc aagttgtagc tactttagtt cctgtccgtc aagtaaaatt tctacgcttc   1380

tgcaagcaac atgctgaagg tgtctgggca gtggtggatg tgtctgttga tgcaatccaa   1440

gagggttcac aaccgcgtga agctggaaac tgcaggaggc tcccctcggg atgtattgtg   1500

caagacttgt ccaatggata ctcaaaggtt atttggattg agcatatgga atatgatgag   1560

agtaccatcc acaattacta ccgcgctttc atcaagtctg gcctgggctt tggtgcccaa   1620

cggtggattg ccgccctaca aaggcaatgc gagtgcttgg caatcatcat gtcttctact   1680

gtgtccagtg gggataacgc agttgttggt cccagtggtc ggagaagtat tgcaatgctg   1740

gctcgacgcg tgacttgcaa cttttgtggt ggggtttgtg gaacctttta caagtgggaa   1800

ccaatccaat cagggagtgg agaggagact aagttgatga tgaggaagag cgttggtgaa   1860

cttggtgagc cttctggtgt gatgttgagt gccaccagga ccatctggct gccgataaca   1920

catcaacgtt tgtttgactt cctgagaaat gcacaaacaa gaaggcaatg ggatgtcttg   1980

ttccatggtg atgccatgca cgaaatagtc cacattgcca agggtcagga tcttggcaat   2040

agcatctctc tctatcgtac taatgtgact ggtagcgatg gtaatcaaag tagtatgttg   2100

tacttgcagg actcctgcac tgatgtgtcg ggttcaattg tatcatatgc agctgttgat   2160

actgcacaaa tgaatgttgt gatgagtggt ggagattcct cctgcgtgac tttcctgcca   2220

tctgggtttg ccatagttcc agattgtttt gggaattcca acggggttac tagcaatgga   2280

atgcttgaaa aagaggataa tgggggtagg aacaaggggt ctttcttgac tgtgggatat   2340

caaatattgg tgaataactt gcctggagga aatctcacta tggagtcggt caacaccatt   2400

aactctttcg tctcccgtac tctggatggt atcaaaacta ttttccggtg caattaa      2457
```

```
<210> SEQ ID NO 7
<211> LENGTH: 819
<212> TYPE: PRT
<213> ORGANISM: Capsicum baccatum

<400> SEQUENCE: 7

Met Ser Phe Gly Gly Phe Ile Gly Ser Ser Ser Gly Gly Asp Gly Gly
1               5                   10                  15

Gly Gly Gly Gly Ser Gly Val Ser Arg Leu Val Gly Asp Ser Pro Tyr
            20                  25                  30

Glu Ala Met Pro Thr Ala Thr Val Ala Gln Ser Gln Leu Ile Thr Ser
        35                  40                  45

Ser Leu Pro Gln Ser Ile Phe Asn Ser Ser Pro Leu Ser Leu Ala Leu
    50                  55                  60

Lys Pro Lys Met Glu Gly Ala Ser Asp Met Ser Leu Leu Ala Glu Asn
65                  70                  75                  80

Phe Gly Ala Val Ala Met Gly Arg Ser Asp Glu Asn Asp Ser Arg Ser
                85                  90                  95

Pro Ser Asp His Leu Asp Gly Gly Gly Ser Gly Asp Asp Met Glu Ala
            100                 105                 110

His Val Gly Ser Ser Ser Arg Lys Lys Lys Tyr His Arg His Thr Pro
        115                 120                 125

Tyr Gln Ile Gln Glu Leu Glu Ala Cys Phe Lys Glu Asn Pro His Pro
    130                 135                 140

Asp Glu Lys Ala Arg Leu Glu Leu Gly Lys Arg Leu Ser Leu Glu Thr
145                 150                 155                 160

Arg Gln Val Lys Phe Trp Phe Gln Asn Arg Arg Thr Gln Met Lys Thr
                165                 170                 175

Gln Leu Glu Arg His Glu Asn Ser Met Leu Lys Gln Glu Asn Asp Lys
            180                 185                 190

Leu Arg Leu Glu Asn Leu Ala Met Lys Glu Ala Met Arg Gly Pro Thr
        195                 200                 205

Cys His Gln Cys Gly Gly Gln Ala Ile Leu Gly Glu Ile His Met Glu
    210                 215                 220

Glu His His Leu Lys Ile Glu Asn Ala Arg Leu Arg Asp Glu Tyr Asn
225                 230                 235                 240

Arg Ile Cys Leu Met Ala Asn Lys Val Leu Gly Arg Pro Leu Ser Ser
                245                 250                 255

Phe Pro Ser Pro Met Pro Ala Gly Met Gly Asn Phe Gly Leu Glu Leu
            260                 265                 270

Ala Val Gly Arg Asn Gly Phe Gly Ala Met Asn Ser Val Asp Ala Ala
        275                 280                 285

Leu Pro Met Gly Leu Asp Phe Gly Asn Gly Ile Ser Ser Ala Thr Ile
    290                 295                 300

Pro Val Ile Ser Pro Arg Pro Ile Pro Asn Met Thr Gly Ile Asp Val
305                 310                 315                 320

Ser Phe Asp Lys Thr Val Leu Met Glu Leu Ala Phe Ala Ala Met Asn
                325                 330                 335

Glu Leu Val Lys Leu Ala Glu Ile Ser Gly Pro Leu Trp Phe Arg Ser
            340                 345                 350

Leu Asp Gly Asn Gly Glu Glu Leu Asn Leu Glu Glu Tyr Ala Arg Ser
        355                 360                 365

Phe Pro Pro Cys Ile Gly Met Lys Pro Ala Asn Phe Thr Ala Glu Ala
```

```
    370                 375                 380

Thr Lys Ala Thr Gly Thr Val Met Ile Asn Ser Leu Ala Leu Val Glu
385                 390                 395                 400

Thr Leu Met Asp Thr Ser Gln Trp Val Asp Thr Phe Ser Ser Ile Val
                405                 410                 415

Gly Arg Thr Ser Ser Met Asn Leu Ile Ser Ser Ser Ser Gly Gly Ser
                420                 425                 430

Arg Asn Gly Asn Leu Gln Leu Ile Gln Ala Glu Phe Gln Val Val Ser
        435                 440                 445

Ala Leu Val Pro Val Arg Gln Val Lys Phe Leu Arg Phe Cys Lys Gln
    450                 455                 460

His Ala Glu Gly Val Trp Ala Val Val Asp Val Ser Val Asp Ala Ile
465                 470                 475                 480

Gln Glu Gly Ser Gln Pro Arg Glu Ala Gly Asn Cys Arg Arg Leu Pro
                485                 490                 495

Ser Gly Cys Ile Val Gln Asp Leu Ser Asn Gly Tyr Ser Lys Val Ile
                500                 505                 510

Trp Ile Glu His Met Glu Tyr Asp Glu Ser Thr Ile His His Tyr Tyr
        515                 520                 525

Arg Ala Phe Ile Lys Ser Gly Leu Gly Phe Gly Ala Gln Arg Trp Ile
    530                 535                 540

Ala Ala Leu Gln Arg Gln Cys Glu Cys Leu Ala Ile Ile Met Ser Ser
545                 550                 555                 560

Thr Val Ser Ser Gly Asp Asn Ala Val Val Ala Pro Ser Gly Arg Arg
                565                 570                 575

Ser Ile Ala Met Leu Ala Arg Arg Val Thr Cys Asn Phe Cys Gly Gly
                580                 585                 590

Val Cys Gly Thr Phe Tyr Lys Trp Glu Pro Ile Gln Ser Gly Ser Gly
        595                 600                 605

Glu Glu Thr Lys Leu Met Met Arg Lys Ser Val Gly Glu Leu Gly Glu
    610                 615                 620

Pro Ser Gly Val Met Leu Ser Ala Thr Arg Thr Ile Trp Leu Pro Ile
625                 630                 635                 640

Thr His Gln Arg Leu Phe Asp Phe Leu Arg Asn Ala Gln Thr Arg Arg
                645                 650                 655

Gln Trp Asp Val Leu Phe His Gly Asp Ala Met His Glu Ile Val His
                660                 665                 670

Ile Ala Lys Gly Gln Asp Leu Gly Asn Ser Ile Ser Leu Tyr Arg Thr
        675                 680                 685

Asn Val Thr Gly Ser Asp Gly Asn Gln Ser Ser Met Leu Tyr Leu Gln
    690                 695                 700

Asp Ser Cys Thr Asp Val Ser Gly Ser Ile Val Ser Tyr Ala Ala Val
705                 710                 715                 720

Asp Thr Ala Gln Met Asn Val Val Met Ser Gly Gly Asp Ser Ser Cys
                725                 730                 735

Val Thr Phe Leu Pro Ser Gly Phe Ala Ile Val Pro Asp Cys Phe Gly
                740                 745                 750

Asn Ser Asp Gly Val Thr Asn Asn Gly Met Leu Glu Lys Glu Asp Asn
        755                 760                 765

Gly Gly Arg Asn Asn Gly Ser Phe Leu Thr Val Gly Tyr Gln Ile Leu
    770                 775                 780

Val Asn Asn Leu Pro Gly Gly Asn Leu Thr Met Glu Ser Val Asn Thr
785                 790                 795                 800
```

```
Ile Asn Ser Phe Val Ser Arg Thr Leu Asp Gly Ile Lys Thr Ile Phe
            805                 810                 815

Arg Cys Asn


<210> SEQ ID NO 8
<211> LENGTH: 2460
<212> TYPE: DNA
<213> ORGANISM: Capsicum baccatum

<400> SEQUENCE: 8

atgagttttg gaggcttcat tggtagtagt agtggtggtg acggtggtgg tggtggtggt     60

tctggggttt cgagattggt gggtgatagt ccatacgaag ccatgcctac tgctactgtt    120

gctcagtcac aacttatcac atcatcttta cctcagtcta tatttaactc ttctccacta    180

tctcttgctc ttaaaccgaa gatggaaggt gcaagtgaca tgagtttgtt agcggaaaat    240

tttggtgctg ttgcaatggg aaggtcggat gagaacgata gcaggtcccc tagtgaccac    300

ttagatggtg gtggatcggg cgatgatatg gaagctcacg ttggtagctc atcgaggaag    360

aagaaatacc ataggcacac tccataccaa attcaagaac ttgaagcttg ttttaaggag    420

aatccacacc ctgatgaaaa agctagactt gaacttggta agaggttgtc gttggaaacc    480

aggcaggtga agttttggtt tcaaaatagg agaactcaga tgaagaccca attggagcgc    540

catgaaaatt caatgttaaa gcaagaaaat gacaaactgc gcctagagaa cctggcaatg    600

aaggaagcta tgagagggcc aacttgccac caatgtggtg gccaagcaat tcttggagaa    660

atacacatgg aagagcatca tttgaagatt gagaatgcta ggctgagaga tgaatacaat    720

aggatctgtc ttatggcgaa caaggttttg ggcaggcctt tgtcatcttt ccctagtcca    780

atgccagctg gaatgggcaa ctttggtttg gaacttgctg ttggaagaaa cggctttggt    840

gctatgaact ctgttgacgc tgcattgcca atgggacttg attttggtaa tggtatctca    900

agtgctacta taccagtgat ttcgcctagg cccatcccca acatgactgg tatagatgta    960

tcctttgata agactgtgtt aatggagctt gcttttgctg ccatgaatga gctggttaag   1020

ctggctgaga tcagtggtcc tctgtggttt agaagcttgg atggaaatgg ggaagagttg   1080

aatcttgagg agtatgctag gtcttttcct ccgtgtattg gcatgaagcc tgccaacttc   1140

acagcagaag caacaaaggc aactggtaca gtgatgatca acagtctggc cttggtggag   1200

actttaatgg acacaagtca atgggtggat acattctcaa gcattgttgg cagaacctct   1260

tcaatgaatt tgatctccag cagctcgggt ggaagcagga atggcaattt gcaattgatc   1320

caagctgagt tccaagttgt atctgcttta gttcctgtcc gtcaagtaaa atttctacgc   1380

ttctgcaagc aacatgctga aggtgtctgg gcagtggtgg atgtgtctgt tgatgcaatc   1440

caagagggtt cacaaccgcg tgaagctgga aactgcagga ggctcccctc gggatgtatt   1500

gtgcaagact tgtccaatgg atactcaaag gttatttgga ttgagcatat ggaatatgat   1560

gagagtacca tccaccatta ctaccgcgct ttcatcaagt ctggcctggg atttggtgcc   1620

caacggtgga ttgccgccct acaaaggcaa tgcgagtgct tggcaatcat catgtcttct   1680

actgtgtcca gtggggataa cgcagttgtt gctcccagtg gtcggagaag tattgcaatg   1740

ctggctcgac gcgtgacttg caacttttgt ggtggggttt gtggaacctt ttacaagtgg   1800

gaaccaatcc aatcagggag tggagaagag actaagttga tgatgcggaa gagcgttggt   1860

gaacttggtg agccttctgg tgtgatgttg agtgccacca ggaccatctg gctgccgata   1920

acacatcagc gtttgtttga cttcctgaga aatgcacaaa caagaaggca atgggatgtc   1980
```

```
ttgttccatg gtgatgccat gcacgaaata gtccacattg ccaagggtca ggatcttggc   2040

aatagcatct ctctctatcg tactaatgtg actggtagcg atggtaatca aagtagtatg   2100

ttgtacttgc aggactcctg cactgatgtg tcaggttcaa ttgtatcata tgcagctgtt   2160

gatactgcac aaatgaatgt tgtgatgagt ggtggagatt cctcctgcgt gactttcctg   2220

ccatctggtt ttgccatagt tccagattgt tttgggaatt ccgacggggt tactaacaat   2280

ggaatgcttg aaaaagagga taatgggggt aggaacaatg ggtctttctt gactgtggga   2340

tatcaaatat tggtgaataa cttgcctgga ggaaatctca ctatggagtc ggtcaacacc   2400

attaactctt tcgtctcccg tactctggat ggtatcaaaa ctattttccg gtgcaattaa   2460
```

```
<210> SEQ ID NO 9
<211> LENGTH: 749
<212> TYPE: PRT
<213> ORGANISM: Solanum melongena

<400> SEQUENCE: 9

Met Ser Phe Gly Gly Phe Ile Gly Ser Ser Ser Gly Gly Lys Gly Ser
1               5                   10                  15

Asp Gly Gly Ser Ser Gly Val Ser Arg Leu Val Ala Asp Ser Ser Tyr
            20                  25                  30

Glu Ala Met Pro Thr Ala Thr Ile Ala Gln Ser Gln Leu Ile Thr Ser
        35                  40                  45

Ser Leu Pro His Ser Met Phe Asn Ser Ser Pro Leu Ser Leu Ala Leu
    50                  55                  60

Lys Pro Lys Met Glu Gly Ala Gly Asp Val Asn Phe Asp Ala Val Ala
65                  70                  75                  80

Met Gly Arg Thr Ser Arg Asp Asp Asp Tyr Glu Ser Ser Ser Phe Lys
                85                  90                  95

Glu Asn Pro His Pro Asp Glu Lys Ala Arg Leu Glu Leu Gly Lys Arg
            100                 105                 110

Leu Ser Leu Glu Ser Arg Gln Thr Gln Met Glu Arg His Glu Asn Ser
        115                 120                 125

Met Leu Lys Gln Glu Asn Asp Lys Leu Arg Ile Glu Asn Ile Ala Met
    130                 135                 140

Lys Glu Ala Met Arg Asn Pro Ala Cys Pro His Cys Gly Gly Pro Ala
145                 150                 155                 160

Ile Leu Gly Glu Ile His Ile Glu Glu His His Leu Lys Ile Glu Asn
                165                 170                 175

Ala Arg Leu Arg Asp Glu Tyr Asn Arg Ile Cys Ala Val Ala Asn Lys
            180                 185                 190

Phe Leu Gly Arg Pro Leu Glu Thr Phe His Ala Pro Ala Pro Met Pro
        195                 200                 205

Ala Gly Met Ala Asn Ser Ala Leu Glu Leu Ala Val Gly Arg Asn Gly
    210                 215                 220

Phe Gly Ala Met Ser Ser Val Asp Thr Ala Leu Pro Met Gly Leu Asn
225                 230                 235                 240

Phe Gly Asn Gly Ile Ser Ile Ser Pro Arg Pro Thr Pro Asn Met Ala
                245                 250                 255

Gly Val Asp Val Ser Tyr Asp Lys Asn Met Leu Ile Glu Leu Ala Phe
            260                 265                 270

Val Ser Met Ala Glu Leu Ile Lys Leu Ala Asp Ile Gly Gly Pro Leu
        275                 280                 285
```

```
Trp Leu Arg Asn Phe Asp Gly Ser Ala Glu Glu Leu Asn Leu Glu Glu
    290                 295                 300

Tyr Ala Arg Ser Phe Pro Pro Cys Ile Gly Met Lys Pro Ala His Phe
305                 310                 315                 320

Thr Ala Glu Ala Thr Lys Ala Ala Gly Thr Val Met Ile Asn Ser Leu
                325                 330                 335

Ala Leu Val Glu Ser Leu Met Asp Thr Ser Arg Trp Met Asp Ile Phe
            340                 345                 350

Ser Ser Ile Val Gly Arg Ser Ser Thr Met Asn Val Ile Ser Asn Ser
        355                 360                 365

Ser Gly Gly Ser Lys Asp Gly Asn Leu Leu Leu Ile Gln Ala Glu Phe
    370                 375                 380

Gln Val Pro Ser Ala Leu Val Pro Val Arg Gln Val Lys Phe Leu Arg
385                 390                 395                 400

Phe Cys Lys Gln His Ala Glu Gly Val Trp Val Val Val Asp Val Ser
                405                 410                 415

Ile Asp Ala Ile Gln Glu Gly Ser Gln Pro Arg Glu Ala Gly Asn Cys
            420                 425                 430

Arg Arg Leu Pro Ser Gly Cys Ile Val Gln Asp Leu Pro Asn Gly Tyr
        435                 440                 445

Ser Lys Val Ile Trp Ile Glu His Thr Glu Tyr Asp Glu Ser Thr Ile
    450                 455                 460

His Asn Tyr Cys Arg Pro Tyr Ile Arg Ser Gly Leu Gly Phe Gly Ala
465                 470                 475                 480

Gln Arg Trp Ile Ala Thr Leu Gln Arg Gln Cys Glu Phe Leu Ala Val
                485                 490                 495

Ile Met Ser Ser Ala Val Pro Ser Gly Asp Asn Ser Val Val Ser Pro
            500                 505                 510

Asn Gly Arg Arg Ser Ile Ala Met Leu Ala Arg Arg Val Thr Arg Asn
        515                 520                 525

Phe Cys Ser Gly Val Cys Ser Thr Tyr Tyr Lys Trp Glu Pro Ile Gln
    530                 535                 540

Ser Gly Ser Ala Glu Glu Ser Lys Leu Ile Met Arg Lys Ala Ile Gly
545                 550                 555                 560

Glu Pro Gly Asp Pro His Gly Met Val Leu Ser Ala Ser Arg Thr Leu
                565                 570                 575

Trp Leu Pro Val Thr His Lys Arg Leu Phe Asp Phe Leu Arg Asn Glu
            580                 585                 590

Gln Thr Arg Ser Gln Trp Asp Val Leu Ser His Gly Gly Ser Met His
        595                 600                 605

Pro Ile Val His Ile Ala Lys Gly Gln Asp Leu Gly Asn Ser Ile Ser
    610                 615                 620

Leu Phe Arg Thr Asn Val Thr Asp Gly Asp Gly Asn Gln Asn Ser Leu
625                 630                 635                 640

Leu Thr Leu Gln Glu Ser Cys Thr Asp Val Ser Gly Ser Ile Ile Ala
                645                 650                 655

Tyr Thr Ser Leu Asp Thr Gly Asp Met Asn Val Val Met Asn Gly Gly
            660                 665                 670

Asp Ser Ser Cys Val Ala Phe Leu Pro Ser Gly Leu Ala Ile Val Pro
        675                 680                 685

Asp Cys Tyr Glu Asn Ser Asn Ser Glu Ser Glu Gly Arg Ser Asn Gly
    690                 695                 700

Ser Leu Leu Thr Val Ala Phe Gln Ile Leu Val Asn Ser Leu Pro Ser
```

```
705                 710                 715                 720

Gly Asn Leu Thr Met Asp Ser Val Asn Thr Val Asn Thr Leu Ile Asn
                725                 730                 735

Arg Thr Val Gln Asn Ile Lys Ile Ala Phe Gln Cys Asn
            740                 745


<210> SEQ ID NO 10
<211> LENGTH: 2250
<212> TYPE: DNA
<213> ORGANISM: Solanum melongena

<400> SEQUENCE: 10

atgagttttg gaggtttcat tgggagtagt agtggaggaa aaggcagtga cggtggtagt     60

tctggggttt caagattggt ggctgatagt tcgtacgaag ccatgcctac tgctactatt    120

gctcagtcac aacttatcac atcatcttta ccccattcaa tgtttaactc ttccccgtta    180

tctcttgcgc ttaaaccaaa gatggaaggt gctggtgacg tgaatttcga tgctgttgcg    240

atgggaagga cctccagaga cgatgactat gagagcagtt cttttaagga gaatccacac    300

cctgatgaga aagcaagact tgaacttggt aagagactat cactggaaag caggcagacc    360

cagatggaac ggcatgagaa ttcgatgctg aaacaagaaa acgataagct ccgtattgaa    420

aacatagcga tgaaggaagc tatgaggaac ccagcttgcc cacattgtgg tggtccagcg    480

attctcgggg agatacatat tgaggagcac catctaaaga tagagaatgc ccgcctaaga    540

gacgaatata ataggatatg cgctgtggcc aataaattct tgggaaggcc tttggaaact    600

ttccatgctc ctgctccaat gccagctggg atggctaatt ctgctctgga gcttgctgtg    660

ggaagaaatg gctttggtgc tatgagctct gttgacactg cattgccaat gggacttaat    720

tttggcaatg gtatctcaat ttcccctagg cccaccccca acatggctgg tgtagatgta    780

tcctatgata agaacatgtt aatagagctt gcttttgttt ccatggctga gctgattaag    840

ctggccgata ttggtggtcc tctgtggctt agaaactttg atggaagtgc agaagaattg    900

aaccttgagg agtatgctag gtctttccct ccatgtattg gcatgaaacc cgcccacttc    960

acagctgaag caacaaaggc agctggtaca gtgatgatca acagtctggc cttggtggag   1020

agtctgatgg acacaagtcg atggatggat atattctcaa gtattgttgg cagaagctct   1080

acaatgaatg tgatctctaa cagctcaggt ggaagcaagg atggcaattt gctcttgatc   1140

caagctgagt tccaagttcc gtctgcttta gttcctgtcc gtcaagtaaa gtttctacgc   1200

ttctgcaagc aacacgctga aggtgtctgg gtagtggtgg atgtatctat tgatgctatc   1260

caagaaggtt cacaaccgcg tgaagctgga aactgcagga gactcccttc tggatgtatt   1320

gtgcaagact tgcccaatgg gtactccaag gttatttgga ttgagcacac ggaatatgat   1380

gagagtacca tccacaatta ctgccgccct tacatcaggt ctggcctggg ctttggtgcc   1440

cagcggtgga ttgccaccct acaaaggcaa tgcgagttct tggcagtcat catgtcttct   1500

gctgtgccca gtggtgataa ttcagttgtt agtcccaatg gtcggagaag tattgcaatg   1560

ctggctcgac gcgtaactcg caacttttgc agtggggttt gttcaaccta ttacaagtgg   1620

gaaccaatcc aatcagggtc tgcagaggag agtaagttga ttatgaggaa ggctattggt   1680

gaacctggtg accctcatgg tatggtgttg agtgcctcca ggaccctctg gctgccggtg   1740

acacataagc gtttgtttga cttccttcga aatgaacaaa caagaagtca atgggatgtg   1800

ttgtcccatg gtggttccat gcacccaata gtccacattg ccaagggtca ggatcttggc   1860

aacagcatct ctctgttccg cactaatgtg actgatggcg atggcaatca aaatagtctc   1920
```

```
ttgaccttgc aggagtcgtg cacggatgta tccggttcca ttatagcata tacatccctt   1980

gatactggag atatgaatgt tgtgatgaat ggtggagact cttcctgcgt ggcgttcctt   2040

ccatcaggac ttgctattgt tccagattgt tacgagaact cgaacagtga aagtgagggt   2100

aggagtaatg ggtctctgtt gacggttgca ttccaaattt tagtgaacag cctgccttca   2160

ggaaatctga cgatggattc ggtgaacact gtgaacaccc tcatcaaccg tacagtgcaa   2220

aatatcaaga ttgcattcca gtgcaattaa                                   2250
```

<210> SEQ ID NO 11
<211> LENGTH: 807
<212> TYPE: PRT
<213> ORGANISM: Solanum pennellii

<400> SEQUENCE: 11

```
Met Ser Phe Gly Gly Phe Ile Gly Ser Ser Ser Gly Gly Asn Gly Gly
1               5                   10                  15

Gly Val Ser Arg Leu Val Gly Asp Thr Ser Tyr Glu Ala Met Pro Thr
            20                  25                  30

Ala Thr Met Ala Gln Ser Gln Leu Ile Thr Ser Ser Leu Ser His Ser
        35                  40                  45

Met Phe Asn Ser Ser Pro Leu Ser Leu Ala Leu Lys Pro Lys Met Glu
    50                  55                  60

Gly Ser Gly Asp Leu Ser Phe Asp Gly Met Gly Arg Asn Ser Arg Asp
65                  70                  75                  80

Asp Glu Tyr Glu Ser Arg Ser Gly Thr Gly Ser Asp Asn Phe Asp Gly
                85                  90                  95

Ile Gly Ser Gly Asp Glu Ile Glu Thr His Ile Gly Ser Ser Ser Lys
            100                 105                 110

Ser Ala Lys Lys Tyr His Arg His Thr Pro Tyr Gln Ile Gln Glu Leu
        115                 120                 125

Glu Ala Cys Phe Lys Glu Asn Pro His Pro Asp Glu Lys Ala Arg Leu
    130                 135                 140

Glu Leu Gly Lys Arg Leu Thr Leu Glu Ser Arg Gln Val Lys Phe Trp
145                 150                 155                 160

Phe Gln Asn Arg Arg Thr Gln Met Lys Thr Gln Met Glu Arg His Glu
                165                 170                 175

Asn Ser Met Leu Lys Gln Glu Asn Asp Lys Leu Arg Ile Glu Asn Ile
            180                 185                 190

Ala Met Lys Glu Ala Met Arg Ser Pro Ala Cys Pro His Cys Gly Gly
        195                 200                 205

Gln Ala Ile Phe Gly Glu Ile His Ile Glu Glu His His Leu Lys Ile
    210                 215                 220

Glu Asn Ala Arg Leu Arg Asp Glu Tyr Ser Arg Ile Cys Val Val Ala
225                 230                 235                 240

Asn Lys Phe Leu Gly Arg Gln Val Glu Ser Val His Gly Pro Met Ser
                245                 250                 255

Ala Gly Met Ala Asn Ser Gly Leu Glu Leu Ala Val Gly Arg Asn Gly
            260                 265                 270

Tyr Gly Ala Met Ser Ser Val Asp Thr Ala Leu Pro Met Gly Leu Asn
        275                 280                 285

Phe Gly Asn Asn Phe Ser Ser Ala Leu Pro Ala Ile Ser Pro Arg Pro
    290                 295                 300

Ala Leu Ser Met Ala Gly Val Asp Val Ser Phe Asp Arg Asn Met Leu
```

```
305                 310                 315                 320

Met Glu Leu Ala Phe Ala Ser Met Asn Glu Leu Ile Lys Leu Ala Asp
                325                 330                 335

Ile Gly Ala Pro Leu Trp Leu Gly Asn Phe Asp Gly Thr Ala Glu Val
            340                 345                 350

Leu Asn Leu Glu Glu Tyr Ala Arg Ser Phe Pro Pro Cys Ile Gly Ile
        355                 360                 365

Lys Pro Ala His Leu Thr Ala Glu Ala Thr Lys Ala Thr Gly Thr Val
    370                 375                 380

Met Ile Asn Ser Leu Thr Leu Val Glu Thr Leu Met Asp Thr Ser Arg
385                 390                 395                 400

Trp Met Asp Ile Phe Ser Cys Ile Val Gly Lys Thr Ser Thr Ile Asn
                405                 410                 415

Val Ile Ser Asn Ser Ser Gly Gly Ser Lys Asp Gly Asn Met Gln Leu
            420                 425                 430

Ile Gln Ala Glu Phe Gln Val Pro Ser Ala Leu Val Pro Val Arg Arg
        435                 440                 445

Val Lys Phe Leu Arg Phe Cys Lys Gln His Ala Glu Gly Val Trp Val
    450                 455                 460

Met Val Asp Val Ser Ile Asp Ala Ile Gln Glu Gly Pro Leu Pro Leu
465                 470                 475                 480

Asp Gly Ser Cys Arg Arg Leu Pro Ser Gly Cys Ile Val Gln Glu Leu
                485                 490                 495

Pro Asn Gly Cys Ser Lys Val Ile Trp Ile Glu His Met Glu Tyr Asp
            500                 505                 510

Glu Ser Val Val His Asn Tyr Tyr His Pro Tyr Ile Arg Ser Gly Leu
        515                 520                 525

Gly Phe Gly Ala Gln Arg Trp Ile Ala Thr Leu Gln Arg Gln Cys Glu
    530                 535                 540

Phe Leu Thr Ile Met Ser Ser Pro Val Pro Ser Gly Asp Asn Ser Val
545                 550                 555                 560

Leu Thr Ser Ser Gly Arg Arg Ser Ile Ala Met Leu Ala Arg Arg Val
                565                 570                 575

Ile Arg His Phe Cys Ile Gly Val Cys Ala Thr Tyr Tyr Asn Trp Glu
            580                 585                 590

Ser Ile Gln Leu Gly Thr Ala Glu Glu Ser Lys Phe Ile Met Arg Lys
        595                 600                 605

Gly Val Gly Glu Pro Gly Asp Leu Asn Gly Met Val Leu Ser Ala Ser
    610                 615                 620

Arg Thr Leu Trp Leu Pro Ile Thr His Gln Arg Leu Phe Asp Phe Leu
625                 630                 635                 640

Arg Asn Glu Gln Met Arg Gly Gln Trp Asp Val Leu Ser Gln Gly Gly
                645                 650                 655

Ser Val His Arg Ile Val His Ile Ala Lys Gly Gln Asp Pro Gly Asn
            660                 665                 670

Ser Ile Thr Leu Phe Arg Thr Thr Val Ala Asn Ser Asp Gly Ser Gln
        675                 680                 685

Asn Ser Leu Leu Thr Leu Gln Glu Ser Cys Thr Asp Val Ser Gly Ser
    690                 695                 700

Ile Ile Ala Tyr Ser Ser Leu Asn Thr Gly Asp Met Asn Ala Val Met
705                 710                 715                 720

Asn Gly Gly Asp Ser Ser Cys Val Thr Phe Leu Pro Ser Gly Phe Ala
                725                 730                 735
```

```
Ile Val Pro Asp Cys Tyr Glu Asn Ser Asn Gly Val Ala Gly Ile Gly
            740                 745                 750

Thr Leu Glu Asn Gly Gly Lys Ile Asn Gly Cys Leu Leu Thr Met Gly
        755                 760                 765

Tyr Gln Val Leu Met Ser Asn Pro Pro Thr Gly Asn Leu Thr Met Asp
    770                 775                 780

Ser Val Asn Thr Val Asp Ser Leu Ile Thr Arg Thr Val Gln Asn Ile
785                 790                 795                 800

Lys Leu Ala Phe Gln Cys Asn
                805


<210> SEQ ID NO 12
<211> LENGTH: 2424
<212> TYPE: DNA
<213> ORGANISM: Solanum pennellii

<400> SEQUENCE: 12

atgagttttg gaggttttat tggaagtagt agcggaggaa acggtggtgg ggtttcaaga     60

ttggtgggtg atacttcata cgaagccatg cctactgcta ctatggctca gtcacagctt    120

atcacatcat ctttatctca ttcaatgttt aactcttcac cgttatctct tgctcttaaa    180

ccgaaaatgg aaggttctgg tgatttgagc tttgatggaa tgggaaggaa ctccagagat    240

gatgagtacg agagcaggtc cgggactggg agtgacaact ttgatggtat tggatcgggt    300

gatgaaattg aaactcacat tggtagctca tccaaatcgg caaagaagta ccataggcac    360

actccatacc aaatccaaga gctggaggct tgctttaagg agaatccaca cccggatgag    420

aaagcaaggc tggaacttgg taagaggttg acattggaaa gcaggcaggt taagttttgg    480

ttccagaaca ggagaaccca aatgaagacc cagatggagc gtcatgaaaa ttcaatgttg    540

aagcaagaga atgataagct tcgcattgag aacatagcga tgaaggaagc gatgagaagc    600

ccagcttgcc cacattgtgg tggtcaggca atttttggtg agatacacat tgaagagcat    660

catttgaaga ttgagaatgc tcggctgaga gatgaataca gtaggatctg tgttgtggca    720

aacaagtttc tgggtaggca ggtggaatct gtccatggtc caatgtcagc tggaatggct    780

aattcaggtt tggaacttgc tgtgggaaga aacggctatg gtgctatgag ttctgttgac    840

actgcattgc caatgggtct taattttggc aataatttct caagtgctct accagctatt    900

tcacctaggc ccgccctgag catggccggt gtagatgtat cctttgatag gaacatgcta    960

atggagcttg cttttgcttc catgaatgag ctgattaagc tggctgatat cggtgctcct   1020

ctgtggcttg gaaactttga tggaactgct gaagtattga accttgagga gtatgccagg   1080

tcttttcctc catgtattgg cattaaacct gcccatttga cagcagaagc aaccaaggca   1140

actggtactg tgatgattaa cagtctgacc ttggtggaga ctctgatgga cacaagtcga   1200

tggatggata tattttcatg cattgttggc aaaacctcta caattaatgt gatctccaac   1260

agctcaggtg gaagcaagga tggcaatatg cagttgatcc aagctgagtt ccaagttcct   1320

tctgctttag ttcctgtccg tcgagtgaag tttctacgct tctgcaagca gcatgctgaa   1380

ggtgtctggg tgatggtgga tgtgtctatt gatgctattc aggaaggtcc actaccgctt   1440

gatggaagtt gcaggaggct tccttcggga tgtatcgtgc aagagttgcc caatgggtgc   1500

tccaaggtta tttggattga gcacatggag tatgatgaga gtgtcgtcca caattactac   1560

cacccttaca tcaggtctgg cctggggttt ggtgcccaac ggtggatcgc caccctacaa   1620

aggcaatgcg agttcttgac aatcatgtct tctcctgtgc ccagtggtga taattcagtg   1680
```

```
cttacttcca gtggacggag aagtattgcg atgcttgctc gacgcgtgat tcgccacttt   1740

tgcattggtg tttgtgcaac ctattacaac tgggaatcaa tccaactagg gactgcagag   1800

gagagtaagt ttattatgag gaagggcgtt ggtgaacctg gtgaccttaa tggtatggtg   1860

ttgagtgcca gcaggaccct ctggctgccg ataacacatc aacgtttgtt tgacttcctg   1920

agaaatgaac agatgagagg tcaatgggat gtgttgtccc agggtggttc cgtgcaccga   1980

atagtccaca ttgccaaggg tcaggatcct ggcaatagca tcactctgtt tcgtactact   2040

gtggctaaca gcgatggtag ccaaaacagc ttgctgacct tgcaagagtc gtgcacagat   2100

gtatctggtt cgatcatagc atattcatca cttaataccg gagacatgaa tgctgtgatg   2160

aatggtggag attcctcctg cgtgacgttc cttccatctg gattcgccat tgttccagat   2220

tgttacgaga attccaacgg ggtagctggc attggaacac tggagaatgg tggtaagatt   2280

aatgggtgcc tattgaccat gggataccag gtactcatga gtaacccgcc tacaggaaat   2340

ctcactatgg attcagtgaa cactgttgac tccctcatca cccgtacagt gcagaacatc   2400

aagcttgctt tccagtgcaa ttaa                                          2424
```

<210> SEQ ID NO 13
<211> LENGTH: 824
<212> TYPE: PRT
<213> ORGANISM: Solanum lycopersicum

<400> SEQUENCE: 13

```
Met Ser Phe Gly Gly Phe Ile Gly Ser Ser Ser Gly Gly Asn Gly Gly
1               5                   10                  15

Gly Val Ser Arg Leu Val Gly Asp Thr Ser Tyr Glu Ala Met Pro Thr
            20                  25                  30

Ala Thr Met Ala Gln Ser Gln Leu Ile Thr Ser Ser Leu Ser His Ser
        35                  40                  45

Met Phe Asn Ser Ser Pro Leu Ser Leu Ala Leu Lys Pro Lys Met Glu
    50                  55                  60

Gly Ser Gly Asp Leu Ser Phe Asp Gly Met Gly Arg Asn Ser Arg Asp
65                  70                  75                  80

Asp Glu Tyr Glu Ser Arg Ser Gly Thr Gly Ser Asp Asn Phe Asp Gly
                85                  90                  95

Val Gly Ser Gly Asp Glu Ile Glu Thr His Ile Gly Ser Ser Ser Lys
            100                 105                 110

Ser Ala Lys Lys Tyr His Arg His Thr Pro Tyr Gln Ile Gln Glu Leu
        115                 120                 125

Glu Ala Phe Phe Lys Glu Ser Pro His Pro Asp Glu Lys Ala Arg Leu
    130                 135                 140

Glu Leu Gly Lys Arg Leu Thr Leu Glu Ser Arg Gln Val Lys Phe Trp
145                 150                 155                 160

Phe Gln Asn Arg Arg Thr Gln Met Lys Thr Gln Met Glu Arg His Glu
                165                 170                 175

Asn Ser Met Leu Lys Gln Glu Asn Asp Lys Leu Arg Ile Glu Asn Ile
            180                 185                 190

Ala Met Lys Glu Ala Met Arg Ser Pro Ala Cys Pro His Cys Gly Gly
        195                 200                 205

Gln Ala Ile Leu Gly Glu Ile His Ile Glu Glu His His Leu Lys Ile
    210                 215                 220

Glu Asn Ala Arg Leu Arg Asp Glu Tyr Ser Arg Ile Cys Val Val Ala
225                 230                 235                 240
```

```
Asn Lys Phe Leu Gly Arg Gln Val Glu Ser Val His Gly Pro Met Ser
                245                 250                 255

Ala Gly Met Ala Asn Ser Gly Leu Glu Leu Ala Val Gly Arg Asn Gly
            260                 265                 270

Tyr Gly Ala Met Asn Ser Val Asp Thr Ala Leu Pro Met Gly Leu Asn
        275                 280                 285

Phe Gly Asn Asn Phe Ser Ser Ala Leu Pro Ala Ile Ser Pro Arg Pro
    290                 295                 300

Ala Leu Ser Met Ala Gly Val Asp Val Ser Phe Asp Arg Asn Met Leu
305                 310                 315                 320

Met Glu Leu Ala Phe Ala Ser Met Asn Glu Leu Ile Lys Leu Ala Asp
                325                 330                 335

Ile Gly Ala Pro Leu Trp Leu Gly Asn Phe Asp Gly Thr Ala Glu Val
            340                 345                 350

Leu Asn Leu Glu Glu Tyr Ala Arg Ser Phe Pro Pro Cys Ile Gly Ile
        355                 360                 365

Lys Pro Ala His Phe Thr Ala Glu Ala Thr Lys Ala Thr Gly Thr Val
    370                 375                 380

Met Ile Asn Ser Leu Thr Leu Val Glu Thr Leu Met Asp Thr Ser Arg
385                 390                 395                 400

Trp Met Asp Ile Phe Ser Cys Ile Val Gly Lys Thr Ser Thr Ile Asn
                405                 410                 415

Val Ile Ser Asn Ser Ser Gly Gly Ser Lys Asp Gly Asn Met Gln Leu
            420                 425                 430

Val Arg Tyr Cys Tyr Phe Gly Gly Ser Arg Pro Phe Tyr Asn Val Leu
        435                 440                 445

Gln Ile Gln Ala Glu Phe Gln Val Pro Ser Ala Leu Val Pro Val Arg
    450                 455                 460

Arg Val Lys Phe Leu Arg Phe Cys Lys Gln His Ala Glu Gly Val Trp
465                 470                 475                 480

Val Met Val Asp Val Ser Ile Asp Ala Ile Gln Glu Gly Pro Val Pro
                485                 490                 495

Leu Asp Gly Ser Cys Arg Arg Leu Pro Ser Gly Cys Ile Val Gln Glu
            500                 505                 510

Leu Pro Asn Gly Cys Ser Lys Val Ile Trp Ile Glu His Met Glu Tyr
        515                 520                 525

Asp Glu Ser Val Thr His Asn Tyr Tyr His Pro Tyr Ile Arg Ser Gly
    530                 535                 540

Leu Gly Phe Gly Ala Gln Arg Trp Ile Ala Thr Leu Gln Arg Gln Cys
545                 550                 555                 560

Glu Phe Ile Thr Val Met Ser Ser Pro Val Pro Ser Gly Asp Asn Ser
                565                 570                 575

Val Leu Ser Ser Ser Gly Arg Arg Ser Ile Ala Met Leu Ala Arg Arg
            580                 585                 590

Val Thr Arg His Phe Cys Asn Gly Val Cys Ala Thr Tyr Tyr Lys Trp
        595                 600                 605

Glu Ser Ile Gln Leu Gly Thr Ala Glu Glu Ser Lys Phe Ile Met Arg
    610                 615                 620

Lys Gly Val Gly Glu Pro Gly Asp Leu Asn Gly Met Val Leu Ser Ala
625                 630                 635                 640

Ser Arg Thr Leu Trp Leu Pro Ile Thr His Glu Arg Leu Ser Asp Phe
                645                 650                 655
```

```
Leu Arg Asn Glu Gln Thr Arg Gly Gln Trp Asp Val Leu Ser Gln Gly
            660                 665                 670

Gly Ser Val His Arg Ile Val His Ile Ala Lys Gly Gln Asp Pro Gly
        675                 680                 685

Asn Ser Ile Thr Leu Phe Arg Thr Thr Val Ala Asn Ser Asp Gly Ser
    690                 695                 700

Gln Asn Gly Leu Leu Thr Leu Gln Glu Ser Cys Thr Asp Val Ser Gly
705                 710                 715                 720

Ser Ile Ile Ala Tyr Thr Ser Leu Asn Thr Gly Asp Met Asn Gly Val
                725                 730                 735

Met Asn Gly Gly Asp Ser Ser Cys Val Thr Phe Leu Pro Ser Gly Phe
            740                 745                 750

Ala Met Val Pro Asp Cys Tyr Glu Asn Ser Asn Gly Val Ala Gly Ile
        755                 760                 765

Gly Thr Leu Glu Asn Gly Gly Lys Met Asn Gly Cys Leu Leu Thr Met
    770                 775                 780

Gly Tyr Gln Val Leu Met Ser Asn Pro Pro Thr Gly Asn Leu Thr Met
785                 790                 795                 800

Asp Ser Val Asn Thr Val Asp Ser Leu Ile Thr Arg Thr Val His Asn
                805                 810                 815

Ile Lys Leu Ala Phe Gln Cys Asn
            820
```

<210> SEQ ID NO 14
<211> LENGTH: 2475
<212> TYPE: DNA
<213> ORGANISM: Solanum lycopersicum

<400> SEQUENCE: 14

```
atgagttttg gaggttttat tggaagtagt agtggaggaa acggtggtgg ggtttcaaga      60

ttggtgggtg atacttcata cgaagccatg cctactgcta ctatggctca gtcacagctt     120

atcacatcat ctttatctca ttcaatgttt aactcttcac cgttatctct tgctcttaaa     180

ccgaaaatgg aaggttctgg tgatttaagc tttgatggaa tgggaaggaa ctccagagat     240

gatgagtacg agagcaggtc tgggactggg agtgacaact ttgatggcgt tggatcgggt     300

gatgaaattg aaactcacat tggtagctca tccaaatcgg caaagaagta ccataggcat     360

actccatacc aaatccaaga gctggaggct ttctttaagg agagtccaca cccggatgag     420

aaagcaaggc tggaacttgg taagaggttg acattggaaa gcaggcaggt taagttctgg     480

ttccagaaca ggagaaccca aatgaagact cagatggagc gtcatgaaaa ttcaatgttg     540

aagcaagaga atgataagct tcgcattgag aacatagcga tgaaggaagc gatgagaagc     600

ccagcttgcc cacattgtgg tggtcaggca attcttgggg agatacacat tgaagagcat     660

catttgaaga ttgagaatgc tcggctgaga gatgaataca gtaggatctg tgttgttgca     720

aacaagtttc tgggtaggca ggtggaatct gtccatggtc caatgtcagc tggaatggct     780

aattcaggtt tggaacttgc tgtgggaaga aacggctatg gtgctatgaa ttctgttgac     840

actgcattgc caatgggtct taattttggc aataatttct caagtgctct accagctatt     900

tcacctaggc ccgccctgag catggccggt gtagatgtat cctttgatag gaacatgcta     960

atggagcttg cttttgcttc catgaatgag ctgattaagc tggctgatat cggtgctcct    1020

ctgtggcttg gaaactttga tggaactgct gaagtattga accttgagga gtatgccagg    1080

tcttttcctc catgtattgg cattaaacct gcccatttca cagcagaagc aaccaaggca    1140
```

-continued

```
actggtactg tgatgattaa cagtctgacc ttggtggaga ctctgatgga cacaagtcga   1200
tggatggata tattttcatg cattgttggc aaaacctcta caattaatgt gatctccaac   1260
agctcaggtg gaagcaagga tggcaatatg caattggtac gttattgtta ttttggtgga   1320
agtcgcccat tctataatgt tttgcagatc caagctgagt tccaagttcc ttctgcttta   1380
gttcctgtcc gtcgagtgaa gtttctacgc ttctgcaagc agcatgctga aggtgtctgg   1440
gtgatggtgg atgtgtctat tgatgctatc caggaaggtc cagtaccgct tgatggaagt   1500
tgcaggaggc ttccttcggg atgtatcgtg caagagttgc ccaatgggtg ctccaaggtt   1560
atttggattg agcacatgga gtatgatgag agtgtcaccc acaattacta ccacccttac   1620
atcaggtctg ggctggggtt tggtgcccaa cggtggatcg ccaccctaca aaggcaatgc   1680
gagttcataa cagtcatgtc ttctcctgtg cccagtggtg ataattcagt gcttagttcc   1740
agtggacgga gaagtattgc gatgcttgct cgacgcgtta ctcgccactt ttgcaatggt   1800
gtttgtgcaa cctattacaa gtgggaatca atccaactgg ggactgcaga ggagagcaag   1860
tttattatga ggaagggcgt tggtgaacct ggcgacctta atggtatggt gttgagtgcc   1920
agcaggaccc tctggctgcc gataacacat gaacgtttgt ctgacttcct gcgaaatgaa   1980
cagacgagag gtcaatggga tgtgttgtcc cagggtggtt ccgtgcaccg aatagtccac   2040
attgccaagg gtcaggatcc tggcaatagc atcactctgt ttcgtactac tgtggctaac   2100
agcgatggta gccaaaacgg tttgctgacc ttgcaagagt cgtgcacaga tgtatctggt   2160
tcgatcatag catatacatc acttaatacc ggagacatga atggtgtgat gaatggtggc   2220
gattcctcct gcgtgacgtt ccttccatct ggattcgcca tggttccaga ttgttacgag   2280
aattccaacg gggtagctgg catcggaaca ctggagaacg gtggtaagat gaatgggtgt   2340
ctattgacca tgggatacca ggtactcatg agtaacccgc ctacaggcaa tctcactatg   2400
gattctgtca acactgttga ctctctcatc acccgtacag tgcacaacat caagcttgct   2460
ttccagtgca attaa                                                    2475
```

SOLANACEOUS PLANT CAPABLE OF STENOSPERMOCARPIC FRUIT FORMATION

CROSS-REFERENCE TO RELATED APPLICATIONS

This application is a National Stage Entry of PCT/EP2019/083605, filed Dec. 4, 2019, which claims priority to EP application No. 18212422.2, filed Dec. 13, 2018, the disclosures of each of which are hereby incorporated by reference in their entireties.

FIELD OF THE INVENTION

This invention relates to the field of plant breeding. In particular to a plant of the family Solanaceae comprising in its genome at least one copy of a mutant allele which causes stenospermocarpic fruit formation when present in homozygous form. The present invention further relates to pollen and seed produced by the plant of the present invention, seed from which the plant of the present invention can be grown and a part from the plant according to the present invention. The present invention further relates to a method of identifying and/or selecting a plant according to the present invention and a method of producing a plant according to the present invention. The present invention further relates to the use of the plant of the present invention as a crop for consumption or as a source of propagation material. The present invention further relates to the use of a nucleic acid for the identification of a plant of the present invention or for breeding plants of the present invention.

BACKGROUND

Most commercial seedless fruits producing plants have been developed in plant species whose fruits normally contain numerous relatively large hard seeds distributed throughout the flesh of the fruit. Seedless fruits are e.g. known for watermelon, cucumber, grapes, banana, citrus fruits, such as orange, lemon and lime, but also from plants of the plant family Solanaceae such as tomato, eggplant and pepper. As consumption of seedless fruits is generally easier and more convenient, they are considered valuable.

Fruit development normally begins when one or more egg cells in the ovular compartment of the flower are fertilized by sperm nuclei from pollen.

Seedless fruits can result from two different phenomena. In some cases fruit develops without fertilization of the ovule by pollen, a phenomenon known as parthenocarpy. In other cases seedless fruits develop after pollination when seed (embryo and/or endosperm) growth is inhibited or the seed dies early, while the remainder of the fruit continues to grow (stenospermocarpy). In contrast to parthenocarpy, stenospermocarpy requires pollination for initiation of fruit growth.

Seedless cucumber, seedless squash and seedless eggplant are examples for crops which can produce seedless fruits without pollination (parthenocarpy), e.g. under conditions where pollination is impaired (e.g. low temperatures). Nevertheless, commercial quality fruit can be produced under these conditions. All these crops however can produce seed bearing fruits upon pollination. Therefore, these crops are facultative parthenocarpic. Propagation of the crops can be done by self- or cross pollination, in vitro propagation, and grafting.

From tomato mutants it is also known that they can produce seedless fruits under conditions where normal pollination/fertilization is impaired (e.g. under circumstances of low temperature). Thus, these mutants are also facultative parthenocarpic. Mutants known for showing this phenotype are pat, pat-2 and the pat-3/pat-4 system (WO1999021411 A1). The genes underlying these mutations are not known and the pat-3/pat-4 system seems to depend on multiple loci.

Parthenocarpy has also been introduced into several plant species by means of genetic modification. Expression of a bacterial tryptophan monooxygenase (iaaM) conferring auxin synthesis under control of the ovule and placenta specific DefH9 promoter did induce parthenocarpy in cucumbers (Yin et al., 2006, Cellular & molecular Biotech. Letters 11, 279-290), eggplant (Acciarri et al., 2002, BMC Biotech. 2(4)), tomato (Rotino et al., 2005, BMC Biotech. 5(32)) and tobacco.

These transgenic plants demonstrate the importance of plant hormones in seed and fruit development. That seed and fruit development are besides other factors strongly under control of several plant hormones is well known in the art. Parthenocarpy, including the logical consequence of fruit's seedlessness, can also be induced e.g. by exogenous application of plant hormones, in particular auxin or gibberellin (Ruan et al., Trends in Plant Sci. 17(11), 1360-1385).

WO2008/152134 A1 describes a male sterile hybrid pepper plant, which grows normal-looking edible seedless fruits throughout the whole plant, wherein said seedless fruits are characterized by being at least 95% seedless. The "seedless" trait of WO2008/152134 A1 is controlled by a genetic determinant obtainable from various pepper plants deposited under the Budapest Treaty which is not further specifically described. WO2008/152134 A1 further describes that the therein disclosed parthenocarpy trait is independent of the pollination and fertilization process, is independent of treatment with parthenocarpy-inducing plant hormones including auxins, gibberellins and cytokines, auxin transport inhibitors, or others and/or other parthenocarpy-inducing exogenous factors and/or exogenously administered parthenocarpy-inducing agents such as growth regulating substances, either natural or synthetic, or plant extracts such as, for example, dead pollen extract, and is also independent of external climatic conditions.

WO2009/098983 A1 describes a seedless fruit-generating pepper plant, wherein said plant is obtained by a specific crossing method. In a first process step the crossing method comprises selecting a first filial generation plant which is capable of bearing seedless fruits as well as having a genetically determined male sterile trait and a genetically determined parthenocarpic trait from the group of first filial generation plants generated by crossing between a plant of a male sterile line and a plant of a parthenocarpic line. In a second process step the thus selected first filial generation plant is then crossed with the "Mi 74 line", which is a specific fixed parthenocarpic line that is capable of sustaining the genetically determined parthenocarpic trait and the genetically determined male sterile trait of the plant, as a pollen parent, to thereby generate a progeny plant having the genetically determined parthenocarpic trait and the genetically determined male sterile trait. In a final process step the thus generated progeny plant is backcrossed again with a plant of the fixed parthenocarpic line used as the pollen parent in the second process step as a pollen parent, to thereby generate a progeny plant having the genetically determined parthenocarpic trait and the genetically determined male sterile trait, wherein the third process step is repeated at least one time.

WO2012/087140 A2 describes a pepper plant comprising a mutated genetic determinant which causes parthenocarpic fruit formation when homozygously present, wherein said genetic determinant is obtainable by introgression from a specific plant grown from seed as deposited under the Budapest Treaty.

WO2013/078319 A1 describes a pepper plant growing parthenocarpic seedless pepper fruits. The pepper plant of WO2013/078319 A1 is obtainable by a method comprising crossing as a female parent a first pepper plant comprising a cytoplasmic male sterile (CMS) trait with a second plant which is parthenocarpic to produce seed of a parthenocarpic seedless pepper plant. The CMS trait of WO2013/078319 A1 is derived from a *Capsicum baccatum* plant.

WO2016/120438 A1 describes that a modified PIN4 protein comprising an amino acid change in the intracellular loop of the protein structure is capable of inducing parthenocarpic fruit set when present in a plant, wherein the plant preferably is a *Cucumis melo, Cucumis sativus, Citrillus lanatus, Solanum lycopersicum, Solanum melongena* or *Capsicum annuum* plant.

WO2017/125931 A1 describes a solanaceous plant selected from the group consisting of tomato, pepper and eggplant exhibiting facultative parthenocarpy and comprising a loss-of-function mutation in the AGL6 gene. The solanaceous plant of WO2017/125931 A1 preferably is a tomato plant.

Seedless watermelon is an example of a stenospermocarp crop. Normal watermelon plants are diploid (2n). Seedless fruit producing watermelons are hybrids produced by crossing a male diploid (2n) watermelon plant with a female tetraploid (4n) watermelon plant. The resulting F1 hybrid seeds are triploid (3n). Induction of fruit setting in the F1 hybrid plants requires pollination. As the triploid (3n) F1 hybrid plants do not produce fertile pollen, diploid (2n) pollinator (or polliniser) plants must be planted in the same field. The cross-pollination between the diploid (2n) pollinator and the flowers of the female triploid (3n) hybrid plant induces fruit set and leads to the production of seedless triploid fruits on the triploid hybrid plant. Generally, a ratio of pollinator to hybrid plants of around 1 to 3 must be planted in a given scheme for providing sufficient pollen for pollinating all the F1 hybrid plants. The diploid (2n) and tetraploid (4n) parents of the F1 hybrid each produce seed bearing fruits and can both be propagated independently from each other by self-pollination.

Seedless grapes can be produced from plants being either parthenocarp or stenospermocarp. The variety Black Corinth is parthenocarp, whereas Sultanina is stenospermocarp. Vine plants are in general propagated by cuttings and successive grafting to another rootstock.

From above discussion it is evident, that the factors determining if plants produce seedless fruits are multiple in nature and can reside in several, e.g. morphologic, physiologic and/or genetic causes.

The solanaceous plants capable of producing seedless fruits according to prior art all are parthenocarp, i.e. they are capable of fruit set in absence of pollination. There are several disadvantages associated with the breeding and cultivation of plants producing seedless fruits as the result of parthenocarpy. Most importantly, parthenocarpic plants in many crops produce fruits having an anomalous shape and/or reduced size. Furthermore, it can be very complex to breed with parthenocarpic plants to introduce the parthenocarpy trait into a different fruit types and varieties in the same plant species as it requires a male sterility background as a prerequisite. Also, the production of F1 hybrid seeds of parthenocarpic plants is often not possible or may be very difficult and inefficient. Accordingly, there is an urgent need to develop improved solanaceous plants capable of producing seedless fruits that have a normal shape and size, wherein the seedless trait can be easily transferred into different fruit types and varieties in the same plant species and for which seeds can be efficiently produced.

Surprisingly a mutant allele could be identified in plants of the family Solanaceae that causes stenospermocarpic fruit formation when present in homozygous form. The wild type gene is designated herein as SSPER-1, for Stenospermocarpy-1. It was further surprisingly found that the seedless fruits produced by plants homozygous for this mutant allele have a normal shape and size. It was further surprisingly found that the mutant allele capable of inducing stenospermocarpic fruit formation can be easily transferred in different fruit types and varieties in the same plant species. It was further surprisingly found that seeds comprising the mutant allele can be efficiently produced, wherein from said seeds plants capable of stenospermocarpic fruit formation can be grown.

SUMMARY OF INVENTION

The present invention relates to a plant of the family Solanaceae comprising in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 70% amino acid sequence identity to SEQ ID NO:1.

The present invention further relates to a seed from which the plant of the present invention can be grown, a plant grown from said seed, a fruit produced by the plant of the present invention, a part of the plant according to the present invention, and a vegetatively propagated plant propagated from a plant part according to the present invention.

In addition, the present invention relates to a method of producing stenospermocarpic fruit comprising growing a plant according to the present invention and harvesting the fruits produced by said plants. The present invention further relates to a method of identifying and/or selecting a plant or plant part of the family Solanaceae comprising a mutant allele of the SSPER-1 gene comprising determining whether the plant or plant part comprises a mutant allele of an SSPER-1 gene, wherein said mutant allele results in reduced expression or no expression of the SSPER-1 gene or wherein the mutant allele encodes a protein having a decreased function or loss-of function when compared to the wild type protein and optionally selecting a plant or plant part comprising at least one copy of a mutant allele of the SSPER-1 gene wherein said mutant allele causes stenospermocarpic fruit formation when present in homozygous form, wherein the wild type SSPER-1 gene encodes a protein comprising at least 70% amino acid sequence identity to SEQ ID NO:1. The present invention further relates to a method of producing a plant of the family Solanaceae comprising in its genome at least one copy of a mutant allele of the SSPER-1 gene as defined herein, wherein said mutant allele causes stenospermocarpic fruit formation when present in homozygous form. The present invention further relates to a method of producing a plant of the family Solanaceae comprising in its genome at least one copy of a mutant allele of the SSPER-1 gene as defined herein, wherein said mutant allele causes stenospermocarpic fruit formation when present in homozygous form, said method comprising the step(s) of: (i) crossing a first Solanaceae plant and a second Solanaceae plant, wherein the first Solanaceae plant is the plant according to the present invention; (ii) optionally harvesting seed from the crossing of (i) and selecting seed comprising in its genome at least one copy of a mutant allele of the SSPER-1 gene as described herein.

In addition, the present invention relates to the use of a plant according to the present invention, preferably comprising a mutant SSPER-1 allele in homozygous form, as a crop for consumption. The present invention further relates to the use of a plant according to the present invention as a source of propagation material. In addition, the present invention relates to the use of a nucleic acid encoding the SSPER-1 protein for the identification of a plant of the family Solanaceae capable of stenospermocarpic fruit formation, wherein said SSPER-1 protein comprises at least 70% amino acid sequence identity to SEQ ID NO:1. The present invention further relates to the use of a nucleic acid encoding the SSPER-1 protein for breeding plants of the family Solanaceae capable of stenospermocarpic fruit formation, wherein said SSPER-1 protein comprises at least 70% amino acid sequence identity to SEQ ID NO:1.

BRIEF DESCRIPTION OF THE SEQUENCE LISTING

SEQ ID NO: 1 shows the amino acid sequence of a wild type *Capsicum annuum* SSPER-1 protein.

SEQ ID NO: 2 shows a nucleotide sequence (coding DNA or cDNA) encoding a wild type *Capsicum annuum* SSPER-1 protein.

SEQ ID NO: 3 shows the amino acid sequence of a mutant *Capsicum annuum* ssper-1 protein.

SEQ ID NO: 4 shows a nucleotide sequence (coding DNA or cDNA) encoding a mutant *Capsicum annuum* ssper-1 protein.

SEQ ID NO: 5 shows the amino acid sequence of a wild type *Capsicum chinense* SSPER-1 protein.

SEQ ID NO: 6 shows a nucleotide sequence (coding DNA or cDNA) encoding a wild type *Capsicum chinense* SSPER-1 protein.

SEQ ID NO: 7 shows the amino acid sequence of a wild type *Capsicum baccatum* SSPER-1 protein.

SEQ ID NO: 8 shows a nucleotide sequence (coding DNA or cDNA) encoding a wild type *Capsicum baccatum* SSPER-1 protein.

SEQ ID NO: 9 shows the amino acid sequence of a wild type *Solanum melongena* SSPER-1 protein.

SEQ ID NO: 10 shows a nucleotide sequence (coding DNA or cDNA) encoding a wild type *Solanum melongena* SSPER-1 protein.

SEQ ID NO: 11 shows the amino acid sequence of a wild type *Solanum pennellii* SSPER-1 protein.

SEQ ID NO: 12 shows a nucleotide sequence (coding DNA or cDNA) encoding a wild type *Solanum penneffii* SSPER-1 protein.

SEQ ID NO: 13 shows the amino acid sequence of a wild type *Solanum lycopersicum* SSPER-1 protein.

SEQ ID NO: 14 shows a nucleotide sequence (coding DNA or cDNA) encoding a wild type *Solanum lycopersicum* SSPER-1 protein.

BRIEF DESCRIPTION OF THE FIGURES

Figure 2:
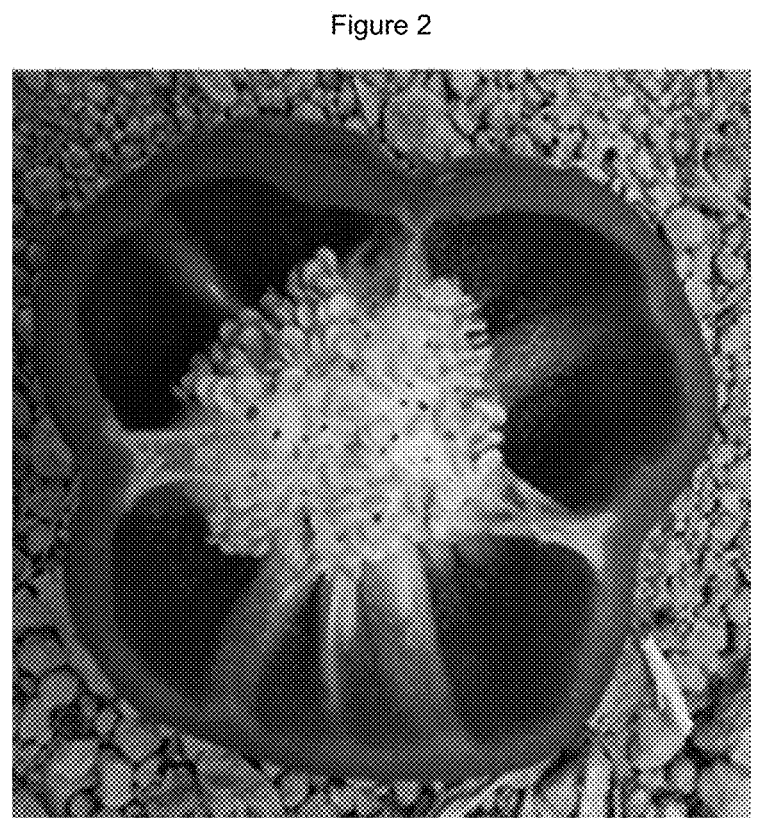

FIG. 2: Greyscale photograph showing the fruit of a sweet bell pepper plant having the same genetic background as the wild type plant (see FIG. 3) with the exception that the plant of FIG. 2 is heterozygous for the mutant allele of the SSPER-1 gene according to the present invention. The fruit shows reduced seed formation in the placenta tissue of the fruit when compared to a fruit from a wild type plant.

DETAILED DESCRIPTION OF THE INVENTION

General Definitions

Figure 1:
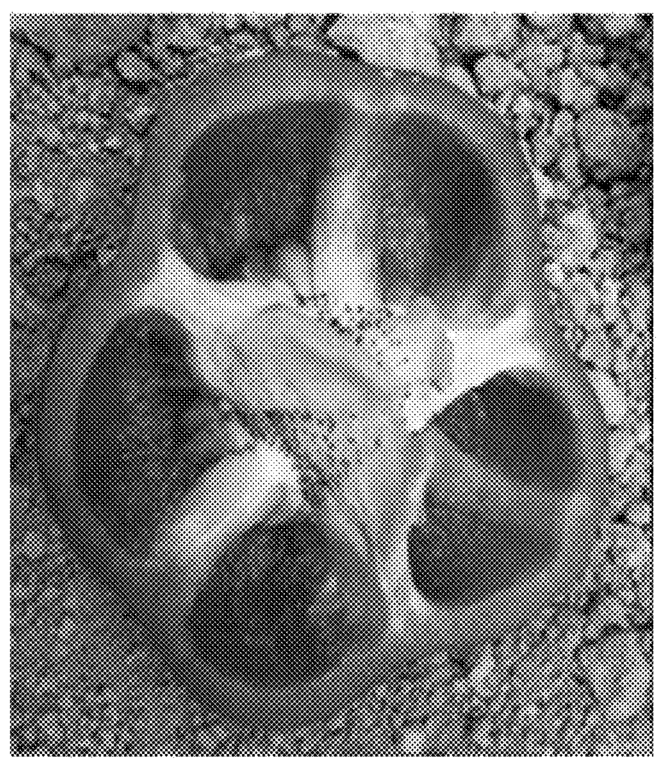
FIG. 1: Greyscale photograph showing the fruit of a sweet bell pepper plant having the same genetic background as the wild type plant (see FIG. 3) with the exception that the plant of FIG. 1 is homozygous for the mutant allele of the SSPER-1 gene according to the present invention. The fruit shows no normal seeds formed, whereas the placenta and septum tissue of the fruits have developed normally, leading to normal fruit shape formation.
Figure 3:
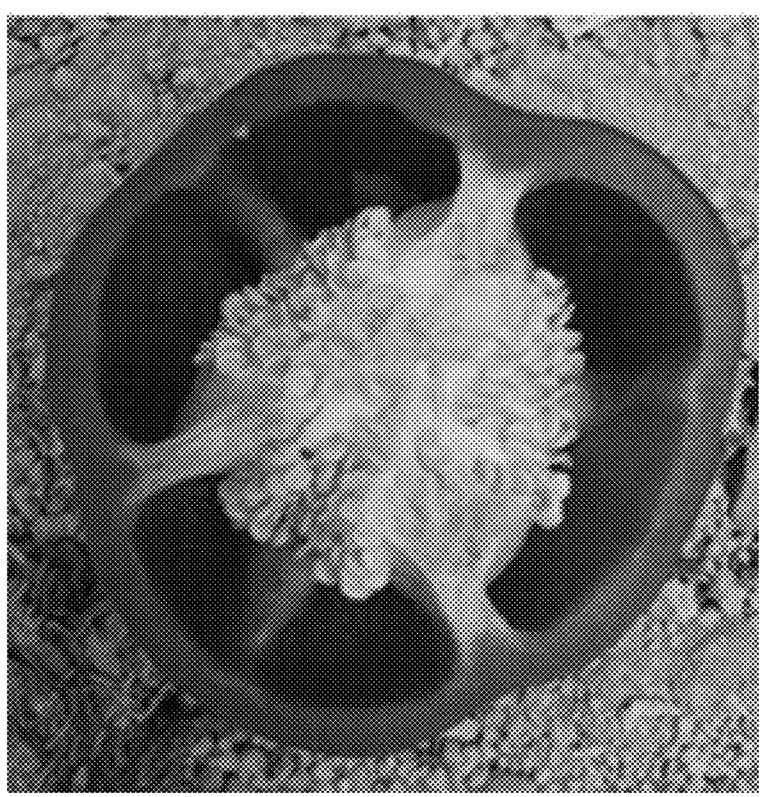
FIG. 3: Greyscale photograph showing the fruit of a wild type sweet bell pepper plant, i.e. a plant the is homozygous for the wild type allele of the SSPER-1 gene. The fruit shows normal seed formation in the placenta tissue of the fruit.

The term "genome" relates to the genetic material of an organism. It consists of DNA. The genome includes both the genes and the non-coding sequences of the DNA.

The term "genetic determinant" relates to the genetic information in the genome of the plant that causes a particular trait of a plant. Accordingly, a genetic determinant comprises the genetic information (gene or locus or introgression) that confers a certain trait. In general, a genetic determinant may comprise a single gene (or one Quantitative Trait Locus (QTL)) or more than one gene. In the present invention, the genetic determinant comprises a single gene.

An allelism test is a test known in the art that can be used to identify whether two genes conferring the same trait are located at the same locus.

The word "trait" in the context of this application refers to the phenotype of the plant. When a plant shows the traits of the invention, its genome comprises the mutant allele causing the trait of the invention, particularly in the present invention when the mutant allele is in homozygous form. The plant, thus, has the genetic determinant of the invention. It is understood that when referring to a plant comprising the trait of the plant of the invention, reference is made to a solanaceous plant comprising the trait of stenospermocarpic fruit formation.

A genetic determinant can be inherited in a recessive manner, an intermediate manner, or in a dominant manner. Selection for the phenotypic trait is easier when intermediate or dominant inheritance is involved, as a larger part of the progeny of a cross reveals the trait. A genetic determinant can also comprise a combination of recessive and/or intermediate and/or dominant genes or QTLs. In the present invention, the genetic determinant comprises a single recessive gene.

Selection for a genetic determinant (e.g. the mutant SSPER-1 allele) can be done on phenotype (the trait that can be observed). Selection can also be done by using molecular genotyping methods, such as one or more molecular markers that are genetically linked to the mutant allele or preferably using the gene or allele sequence itself, e.g. by molecular methods which are able to distinguish between the presence of a mutant allele and wild type allele, or products thereof (such as mRNA or protein encoded by the allele). The use of molecular genotyping methods in breeding (such as "marker assisted selection" when genetically linked markers are used, or other genotyping methods, such as SNP genotyping) requires a smaller population for screening (when compared to phenotypical selection) and can be done in a very early stage. A further advantage of molecular genotyping methods is the possibility to easily distinguish between homozygous plants or seeds having no wild type copies of the SSPER-1 gene (homozygous for the mutant ssper-1 allele), heterozygous plants or seeds and homozygous plants or seeds having no copies of the mutant SSPER-1 gene of the present invention, which can be done even before seeds germinate or in early plant development, e.g. before mature fruits have developed.

A "plant line" or "breeding line" refers to a plant and its progeny. As used herein, the term "inbred line" refers to a plant line which has been repeatedly selfed and is nearly homozygous for every characteristic. Thus, an "inbred line" or "parent line" refers to a plant which has undergone several generations (e.g. at least 5, 6, 7 or more) of inbreeding, resulting in a plant line with a high uniformity.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (plural loci) means a specific place or places or a site on a chromosome where for example a gene or genetic marker is found. The seedless locus (or loci) is thus the location(s) in the genome of a solanaceous plant where the SSPER-1 gene is found.

The term "gene" means a (genomic) DNA sequence comprising a region (transcribed region), which is transcribed into a messenger RNA molecule (mRNA) in a cell, and an operably linked regulatory region (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein. A gene may be an endogenous gene (in the species of origin) or a chimeric gene (e.g. a transgene or cis-gene). The "promoter" of a gene sequence is defined as a region of DNA that initiates transcription of a particular gene. Promoters are located near the genes they transcribe, on the same strand and upstream on the DNA. Promoters can be about 100-1000 base pairs long. In one aspect the promoter is defined as the region of about 1000 base pairs or more e.g. about 1500 or 2000, upstream of the start codon (i.e. ATG) of the protein encoded by the gene.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment.

A "quantitative trait locus", or "QTL" is a chromosomal locus that encodes for one or more alleles that affect the expressivity of a continuously distributed (quantitative) phenotype.

"Physical distance" between loci (e.g. between molecular markers and/or between phenotypic markers) on the same chromosome is the actual physical distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Wild type allele" (WT) refers herein to a version of a gene encoding a fully functional protein (wild type protein). Accordingly, the term "wild type SSPER-1 allele" or "SSPER-1 allele" or "wild type allele of the SSPER-1 gene" refers to the fully functional allele of the SSPER-1 gene, which allows the normal formation of mature and/or viable seeds in the fruit. Such a wild type SSPER-1 allele in the species *Capsicum annuum* for instance is the wild type genomic DNA which encodes the wild type SSPER-1 cDNA (mRNA) sequence depicted in SEQ ID NO:2. The protein sequence encoded by this wild type *Capsicum annuum* SSPER-1 cDNA has 815 amino acids and is depicted in SEQ ID NO:1, which corresponds to NCBI reference sequence XP_016564676.1. A wild type SSPER-1 allele in the species *Capsicum chinense* for instance is the wild type genomic DNA which encodes the wild type SSPER-1 cDNA (mRNA) sequence depicted in SEQ ID NO:6. The protein sequence encoded by this wild type *Capsicum chinense* SSPER-1 cDNA has 818 amino acids and is depicted in SEQ ID NO: 5, which corresponds to NCBI reference sequence PHU23006.1. A wild type SSPER-1 allele in the species *Capsicum baccatum* for instance is the wild type genomic DNA which encodes the wild type SSPER-1 cDNA (mRNA) sequence depicted in SEQ ID NO:8. The protein sequence encoded by this wild type *Capsicum baccatum* SSPER-1 cDNA has 819 amino acids and is depicted in SEQ ID NO:7, which corresponds to NCBI reference sequence PHT53105.1. A wild type SSPER-1 allele in the species *Solanum melongena* for instance is the wild type genomic DNA which encodes the wild type SSPER-1 cDNA (mRNA) sequence depicted in SEQ ID NO:10. The protein sequence encoded by this wild type *Solanum melongena* SSPER-1 cDNA has 749 amino acids and is depicted in SEQ ID NO:9, which corresponds to GenBank accession GBGZ01086676.1. A wild type SSPER-1 allele in the species *Solanum* pennellii for instance is the wild type genomic DNA which encodes the wild type SSPER-1 cDNA (mRNA) sequence depicted in SEQ ID NO:12. The protein sequence encoded by this wild type *Solanum* pennellii SSPER-1 cDNA has 807 amino acids and is depicted in SEQ ID NO:11, which corresponds to NCBI reference sequence XP_015070591.1. A wild type SSPER-1 allele in the species *Solanum lycopersicum* for instance is the wild type genomic DNA which encodes the wild type SSPER-1 cDNA (mRNA)

sequence depicted in SEQ ID NO:14. The protein sequence encoded by this wild type *Solanum lycopersicum* SSPER-1 cDNA has 824 amino acids and is depicted in SEQ ID NO:13, which corresponds to NCBI reference sequence XP_004234441.1. In further plant species of the family Solanaceae one or more orthologs of the herein specifically described wild type SSPER-1 alleles can be identified using methods known in the art. The wild type SSPER-1 allele further comprises functional variants of the wild type genomic DNA which encodes the wild type SSPER-1 cDNA and amino acid sequences as described herein. Whether a certain variant of the herein specifically described wild type SSPER-1 allele represents a functional variant can be determined by using routine methods, including, but not limited to, phenotypic testing for normal formation of mature and/or viable seeds in the fruit and in silico prediction of amino acid changes that affect protein function. For instance, a web-based computer program SIFT (Sorting Intolerant From Tolerant) is a program that predicts whether an amino acid substitution affects protein function; see world wide web at sift.bii.a-star.edu.sg/. Functionally important amino acids will be conserved in the protein family, and so changes at well-conserved positions tend to be predicted as not tolerated or deleterious; see also Ng and Henikoff (2003) Nucleic Acids Res 31(13): 3812-3814. For example, if a position in an alignment of a protein family only contains the amino acid isoleucine, it is presumed that substitution to any other amino acid is selected against and that isoleucine is necessary for protein function. Therefore, a change to any other amino acid will be predicted to be deleterious to protein function. If a position in an alignment contains the hydrophobic amino acids isoleucine, valine and leucine, then SIFT assumes, in effect, that this position can only contain amino acids with hydrophobic character. At this position, changes to other hydrophobic amino acids are usually predicted to be tolerated but changes to other residues (such as charged or polar) will be predicted to affect protein function. An alternative tool useful for the prediction of protein function is Provean; see world wide web at provean.jcvi.org/index.php.

"Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different 3D conformation, being targeted to a different sub-cellular compartment, having a modified catalytic domain, having a modified binding activity to nucleic acids or proteins, etc. Mutant alleles according to the invention can be generated by mutagenesis methods, such as chemical mutagenesis (e.g. using EMS or MNU mutagenesis or mutagenesis by generating reactive oxygen species) or other radiation mutagenesis (e.g. using UV radiation or ion beam radiation) Accordingly, "mutant ssper-1 allele" or "ssper-1 allele" or "mutant allele of the SSPER-1 gene" refers to an allele of the SSPER-1 gene comprising one or more mutations in the coding sequence compared to the wild type allele, which one or more mutations leads to a reduced function or loss-of-function of encoded gene product and which precludes the normal formation of mature and/or viable seeds in the fruit when the mutant allele is in homozygous form. Such a mutant type ssper-1 allele in the species *Capsicum annuum* for instance is the mutant ssper-1 cDNA (mRNA) sequence depicted in SEQ ID NO:4. The protein sequence encoded by this mutant *Capsicum annuum* ssper-1 cDNA has 181 amino acids and is depicted in SEQ ID NO:3. Preferably, the term mutant ssper-1 allele as used herein refers herein to any allele of the wild type SSPER-1 gene or ssper-1 allele which is not found in plants in the natural population or breeding population, but which is produced by human intervention such as mutagenesis or targeted gene modification (also referred to as targeted gene editing), such as effected through e.g. CRISPR/Cas9, CRISPR/Cpf1 or similar methods. The term mutant ssper-1 allele also comprises knock-out ssper-1 alleles and knock-down ssper-1 alleles, as well as ssper-1 alleles encoding a SSPER-1 protein having reduced function or no function. As used herein, the term "knock-out allele" refers to an allele wherein the expression of the respective (wild type) gene is not detectable anymore. A "knock-down" ssper-1 allele has reduced expression of the respective (wild type) gene compared to the wild type allele.

"Wild type plant" refers herein to a plant of the family Solanaceae comprising two copies of the wild type SSPER-1 allele showing normal formation of mature and/or viable seeds in the fruit. Such plants are for example suitable controls in phenotypic essays.

In a plant of the family Solanaceae the wild type SSPER-1 gene encodes a protein comprising at least 70% (71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7%) amino acid sequence identity to SEQ ID NO:1. The protein described by the amino acid sequence SEQ ID NO:1 represents the wild type SSPER-1 protein in *Capsicum annuum* and corresponds to NCBI reference sequence XP_016564676.1. In other plants of the family Solanaceae the wild type SSPER-1 protein accordingly is encoded by an ortholog of the wild type SSPER-1 gene in *Capsicum annuum*. Preferably, the ortholog of the *Capsicum annuum* SSPER-1 gene in other plants of the family Solanaceae encodes a protein having at least 65% (e.g. at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7%) amino acid sequence identity to SEQ ID NO:1.

The term "orthologous gene" or "ortholog" is defined as genes in different species that have evolved through speciation events. It is generally assumed that orthologs have the same biological functions in different species. Accordingly, it is particularly preferred that the protein encoded by the ortholog of the wild type *Capsicum annuum* SSPER-1 gene in in other plants of the family Solanaceae has the same biological function as the wild type *Capsicum annuum* SSPER-1 protein. Methods for the identification of orthologs is very well known in the art as it accomplishes two goals: delineating the genealogy of genes to investigate the forces and mechanisms of evolutionary process and creating groups of genes with the same biological functions (Fang G, et al (2010) Getting Started in Gene Orthology and Functional Analysis. PLoS Comput Biol 6(3): e1000703. doi:10.1371/journal.pcbi.1000703). For instance, orthologs of a specific gene or protein can be identified using sequence alignment or sequence identity of the gene sequence of the protein of interest with gene sequences of other species. Gene alignments or gene sequence identity determinations can be done according to methods known in the art, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, FASTA, etc.). In one aspect of the invention an ortholog of the *Capsicum annuum* SSPER-1 protein in other plants of the family Solanaceae has at least least 65% (e.g. at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7%) amino acid sequence identity with SEQ ID NO: 1.

The wild type SSPER-1 protein comprises several distinct conserved domains comprising, but not limited to a DNA-binding homeobox domain and a lipid-binding START domain. In the wild type SSPER-1 protein in *Capsicum annuum* the DNA-binding homeobox domain comprises amino acid residues starting at, and including, amino acid 118 and ending at, and including, amino acid 171 (indicated herein as amino acids 118-171) of SEQ ID NO:1. The lipid-binding START domain in the wild type SSPER-1 protein in *Capsicum annuum* comprises amino acid residues 320-548 of SEQ ID NO:1. These conserved domains are believed to be important for the in vivo activity of the protein.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). It is understood that the term "introgression fragment" never includes a whole chromosome, but only a part of a chromosome. The introgression fragment can be large, e.g. even three-quarters or half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

The term "isogenic plant" refers to two plants which are genetically identical except for the mutant allele of the present invention. In order to investigate the impact of the stenospermocarpic fruit formation trait, one can cross a plant line (or variety) of interest with a plant comprising the mutant allele causing the stenospermocarpic fruit formation trait and select for progeny expressing the desired trait. Optionally one may have to self the progeny one or more times to be able to determine the genetic determinants for the stenospermocarpy trait in the plant phenotype. Said progeny can then be backcrossed (at least 2 times, e.g. 3, 4, or preferably 5 or 6 times) with the plant line (or variety) of interest while selecting for progeny having the same phenotype as the plant line (or variety) of interest and expressing the genetic determinants for the stenospermocarpy trait. The impact of the mutant allele causing the stenospermocarpic fruit formation trait can then be compared between the plant line (variety) of interest and its isogenic line not comprising the genetic determinants for the stenospermocarpic fruit formation trait.

The term "nucleic acid sequence" or "nucleic acid molecule" or polynucleotide are used interchangeably and refer to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein", "peptide sequence", "amino acid sequence" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

An "active protein" or "functional protein" is a protein which has protein activity as measurable in vitro, e.g. by an in vitro activity assay, and/or in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation results in (the mutant nucleic acid molecule encoding) a protein having altered activity.

"Functional derivatives" of a protein as described herein are fragments, variants, analogues, or chemical derivatives of the protein which retain at least a portion of the activity or immunological cross reactivity with an antibody specific for the mutant protein.

A fragment of a mutant protein refers to any subset of the molecule.

Variant peptides may be made by direct chemical synthesis, for example, using methods well known in the art.

An analogue of a mutant protein refers to a non-natural protein substantially similar to either the entire protein or a fragment thereof.

A "mutation" in a nucleic acid molecule is a change of one or more nucleotides compared to the wild type sequence, e.g. by replacement, deletion or insertion of one or more nucleotides.

A "mutation" in an amino acid molecule making up a protein is a change of one or more amino acids compared to the wild type sequence, e.g. by replacement, deletion or insertion of one or more amino acids. Such a protein is then also referred to as a "mutant protein".

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a pre-mature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid at either the N-terminus or the C-terminus of the protein is missing compared to the amino acid sequence of the corresponding wild type protein, whereby in a 3'-end or C-terminal truncation at least the first nucleotide at the 5'-end or the first amino acid at the N-terminus, respectively, is still present and in a 5'-end or N-terminal truncation at least the last nucleotide at the 3'-end or the last amino acid at the C-terminus, respectively, is still present. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the nucleic acid sequences being linked are typically contiguous.

"Sequence identity" and "sequence similarity" can be determined by alignment of two peptide or two nucleotide sequences using global or local alignment algorithms. Sequences may then be referred to as "substantially identical" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, (as available on the Internet by ebi.ac.uk at http://www.ebi-.ac.uk under/Tools/psa/emboss_needle/). Alternatively, sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% (as determined by Emboss "needle" using default parameters, i.e. gap creation penalty=10, gap extension penalty=0.5, using scoring matrix DNAFULL for nucleic acids and Blosum62 for proteins). Such sequences are also referred to as 'variants' herein, e.g. other variants of alleles causing the stenospermocarpic fruit formation trait and proteins than the specific nucleic acid and amino acid sequences disclosed herein can be identified, which have the same effect on stenospermocarpic fruit formation as the plants of the present invention.

The term "hybridisation" as used herein is generally used to mean hybridisation of nucleic acids at appropriate conditions of stringency (stringent hybridisation conditions) as would be readily evident to those skilled in the art depending upon the nature of the probe sequence and target sequences. Conditions of hybridisation and washing are well-known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, New York, 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C., 0.01 M EDTA, 1×Denhardt's solution and 0.5% SOS. hybridisation is carried out at about 68° C. for about 3 to 4 hours for fragments of cloned DNA and for about 12 to about 16 hours for total eukaryotic DNA. For lower stringencies the temperature of hybridisation is reduced to about 42° C. below the melting temperature (T M) of the duplex. The T M is known to be a function of the G-C content and duplex length as well as the ionic strength of the solution.

As used herein, the phrase "hybridizes" to a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridisation under appropriate conditions. For example, a 100 nucleotide long molecule from the 3' coding or non-coding region of a gene will recognize and hybridize to an approximately 100 nucleotide portion of a nucleotide sequence within the 3' coding or non-coding region of that gene or any other plant gene so long as there is about 70% or more sequence similarity between the two sequences. It is to be understood that the size of the corresponding portion will allow for some mismatches in hybridisation such that the corresponding portion may be smaller or larger than the molecule which hybridizes to it, for example 20-30% larger or smaller, preferably no more than about 12-15% larger or smaller.

As used herein, the phrase "a sequence comprising at least 70% sequence identity" or "a sequence comprising at least 70% amino acid sequence identity" or "a sequence comprising at least 70% nucleotide sequence identity" means a sequence having at least 70% e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity when compared with the reference sequence that is indicated. Sequence identity can be determined according the methods described herein.

In accordance with the above provided definition, an ortholog or orthologous sequence of a genetic determinant, which in the context of the present invention is a mutant allele of the wild type SSPER-1 gene, refers to a stenospermocarpic fruit formation conferring allele in a different Solanaceae species than *Capsicum annuum*, e.g. a mutant allele of an ortholog of the *Capsicum annuum* SSPER-1 gene in another species of the family Solanaceae which mutant allele causes stenospermocarpic fruit formation when in homozygous form in that species, i.e. an ortholog of the mutant allele of the present invention, and wherein the orthologous genomic sequence encoded by the gene comprises substantial sequence identity to nucleic acid as described by SEQ ID NO:4, i.e. at least 65% (e.g. at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7%) sequence identity or more and/or the orthologous amino acid sequence encoded by the gene comprises substantial sequence identity to the amino acid sequence of SEQ ID NO: 3, i.e. at least 65% (e.g. at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7%) sequence identity or more.

A "fragment" of the gene or DNA sequence refers to any subset of the molecule, e.g., a shorter polynucleotide or oligonucleotide. In one aspect the fragment comprises the mutation as defined by the invention.

A "variant" of the gene or DNA refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. Preferably the variant comprises the mutant allele as defined by the invention.

As used herein, the term "plant" includes the whole plant or any parts or derivatives thereof, such as plant organs (e.g., harvested or non-harvested flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries (e.g., harvested tissues or organs), flowers, leaves, seeds, tubers, clonally propagated plants, roots, stems, cotyledons, hypocotyls, root tips and the like. Also any developmental stage is included, such as seedlings, immature and mature, etc. Preferably the plant part or derivative comprises the gene or locus as defined by the current invention.

A "plant line" or "breeding line" refers to a plant and its progeny.

"Plant variety" is a group of plants within the same botanical taxon of the lowest grade known, which (irrespective of whether the conditions for the recognition of plant breeders rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc. "F1 hybrid" plant (or F1 seed, or hybrid) is the generation obtained from crossing two inbred parent lines. "Selfing", accordingly, refers to the self-pollination of a plant, i.e. to the union of gametes from the same plant.

"Backcrossing" refers to a breeding method by which a (single) trait, such as the capability for stenospermocarpic fruit formation, can be transferred from one genetic background (also referred to as "donor" generally, but not necessarily, this is an inferior genetic background) into another genetic background (also referred to as "recurrent parent"; generally, but not necessarily, this is a superior genetic background). An offspring of a cross (e.g. an F1 plant obtained by crossing a first plant of a certain plant species comprising the mutant allele of the present invention with a second plant of the same plant species or of a different plant species that can be crossed with said first plant species wherein said second plant species does not comprise the mutant allele of the present invention; or an F2 plant or F3 plant, etc., obtained by selfing the F1) is "backcrossed" to a parent plant of said second plant species. After repeated backcrossing, the trait of the donor genetic background, e.g. the mutant allele conferring the stenospermocarpic fruit formation trait, will have been incorporated into the recurrent genetic background. The terms "gene converted" or "conversion plant" or "single locus conversion" in this context refer to plants which are developed by backcrossing wherein essentially all of the desired morphological and/or physiological characteristics of the recurrent parent are recovered in addition to the one or more genes transferred from the donor parent. The plants grown from the seeds produced by backcrossing of the F1 plants with the second parent plant line is referred to as the "BC1 generation". Plants from the BC1 population may be selfed resulting in the BC1F2 generation or backcrossed again with the cultivated parent plant line to provide the BC2 generation. An "M1 population" is a plurality of mutagenized seeds/plants of a certain plant line. "M2, M3, M4, etc." refers to the consecutive generations obtained following selfing of a first mutagenized seed/plant (M1).

"Solanaceous plants" or "plants of the family Solanaceae" are plants of the botanical family Solanaceae, i.e. any plant of the family Solanaceae, including wild solanaceous plants and cultivated solanaceous plants. The botanical family Solanaceae consists about 98 genera of which the genera *Solanum* and *Capsicum* are the commercially most relevant as they comprise many domesticated species that are widely cultivated and used as food crops with high economic importance.

The genus *Capsicum* consists of 20 to 27 species, five of which are domesticated: *C. annuum, C. baccatum, C. chinense, C. frutescens*, and *C. pubescens*. Phylogenetic relationships between species have been investigated using bio-geographical, morphological, chemosystematic, hybridization, and genetic data. Fruits of *Capsicum*, often named as "peppers" or "pepper fruits", can vary tremendously in color, shape, and size both between and within species. Chemosystematic studies helped distinguish the difference between varieties and species.

*Capsicum annuum* L. plants are herbaceous plants of the family Solanaceae that are of particular relevance in the context of the present invention. *Capsicum annuum* plants reach about 0.5-1.5 meters (about 20-60 inches). Single white flowers bear the pepper fruit which is green when unripe, changing principally to red, although some varieties may ripen to brown or purple. While the species can tolerate most climates, they are especially productive in warm and dry climates. Cultivated plants of the species *Capsicum annuum* include different types of peppers, such as bell peppers, cayenne peppers, paprika, and jalapeños. "*Capsicum annuum* chromosome 3" refer to the *Capsicum annuum* chromosome 3, as known in the art (see *Capsicum annuum* cv CM334 genome chromosomes (release 1.55) and *Capsicum annuum* UCD10X genome chromosomes (v1.0) and *Capsicum annuum* zunla genome chromosomes (v2.0) "Orthologous chromosome 3" refers to the corresponding chromosome of relatives of *Capsicum annuum*.

The genus *Solanum* consists of about 1330 species, including the highly important food crops *S. lycopersicum* (tomato), *S. melongena* (eggplant) and *S. tuberosum* (potato).

*Solanum lycopersicum* plants or "tomato plants" are further herbaceous plants of the family Solanaceae that are of particular relevance in the context of the present invention. Tomato plants are perennial in their native habitat but cultivated as an annual. Cultivated tomato plants typically grow to 1-3 meters (3-10 ft) in height. Tomato fruits are botanically berry-type fruits, they are considered culinary vegetables. Fruit size varies according to cultivar, with a width range of about 1-10 cm (about 0.5-4 inches). *Solanum lycopersicum* is also known as *Lycopersicon lycopersicum* (L.) H. Karst. or *Lycopersicon esculentum* Mill. The term "cultivated tomato plant" or "cultivated tomato" refers to plants of *Solanum lycopersicum*, e.g. varieties, breeding lines or cultivars of the species *S. lycopersicum*, cultivated by humans and having good agronomic characteristics. "Wild relatives of tomato" include *S. arcanum, S. chmielewskii, S. neorickii* (=*L. parviflorum*), *S. cheesmaniae, S. galapagense, S. pimpinellifolium, S. chilense, S. corneliomulleri, S. habrochaites* (=*L. hirsutum*), *S. huaylasense, S. sisymbriifolium, S. peruvianum, S. hirsutum* or *S. pennellii*. Tomato and the wild relatives of tomato is/are diploid and has/have 12 pairs of homologous chromosomes, numbered 1 to 12.

*Solanum melongena* plants or "eggplant" or "aubergine plants" are further herbaceous plants of the family Solanaceae that are of particular relevance in the context of the present invention. The egg-shaped, glossy, dark purple to white fruit has white flesh with a meaty texture. *S. melongena* plants grow about 40-150 cm (about 1.3-5 ft) tall, with large, coarsely lobed leaves that are about 10-20 cm (about 3-8 in) long and about 5-10 cm (about 2-4 in) broad.

The term "cultivated plant" or "cultivar" refers to plants of a given species, e.g. varieties, breeding lines or cultivars of the said species, cultivated by humans and having good agronomic characteristics. The so-called heirloom varieties or cultivars, i.e. open pollinated varieties or cultivars commonly grown during earlier periods in human history and often adapted to specific geographic regions, are in one aspect of the invention encompassed herein as cultivated plants. The term "cultivated plant" does not encompass wild plants. "Wild plants" include for example wild accessions.

The term "food" is any substance consumed to provide nutritional support for the body. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth. The term food includes both substance consumed to provide nutritional support for the human and animal body.

"Vegetative propagation" or "clonal propagation" refers to propagation of plants from vegetative tissue, e.g. by propagating plants from cuttings or by in vitro propagation. In vitro propagation involves in vitro cell or tissue culture and regeneration of a whole plant from the in vitro culture. Clones (i.e. genetically identical vegetative propagations) of the original plant can thus be generated by in vitro culture. "Cell culture" or "tissue culture" refers to the in vitro culture of cells or tissues of a plant. "Regeneration" refers to the development of a plant from cell culture or tissue culture or vegetative propagation. "Non-propagating cell" refers to a cell which cannot be regenerated into a whole plant.

"Average" refers herein to the arithmetic mean.

It is understood that comparisons between different plant lines involves growing a number of plants of a line (or variety) (e.g. at least 5 plants, preferably at least 10 plants per line) under the same conditions as the plants of one or more control plant lines (preferably wild type plants) and the determination of statistically significant differences between the plant lines when grown under the same environmental conditions. Preferably the plants are of the same line or variety.

The term "stenospermocarpy" or "stenospermocarpic fruit formation" is generally understood in the art, and also to be understood in connection with the present invention, to mean that induction of fruit set and development requires pollination but without the fruits producing mature or viable seeds. Mature or viable seeds are not developed in stenospermocarpic plants due to arrested seed development or degradation of ovules and/or embryos and/or endosperm or abortion of the ovules and/or embryos and/or endosperm before maturity is reached. The term "parthenocarpy" or "parthenocarpic fruit formation" is generally understood in the art, and also to be understood in connection with the present invention, to describe the development of fruits without fertilization of the female ovule. A pollination process is not needed for producing fruits, which fruits are seedless because of the lack of pollination. The term "plant capable of stenospermocarpic fruit formation" or "plant having stenospermocarpy trait" as used herein accordingly describes a plant that develops fruits wherein the induction of fruit set and development requires pollination but without the fruits producing mature or viable seeds. A "seedless fruit" as commonly used in the art and in particular in breeding, although being somehow contradicting the botanical meaning of "fruit", is to be understood in context with the present invention to be a fruit substantially without mature or viable seeds. Mature or viable seeds can be germinated in soil under conditions appropriate for the respective plant and grown into plants. This test can be used to determine if a plant produces seedless fruits. Seedless fruits will produce substantially no seed which will germinate and grow into a plant under conditions appropriate for the respective plant. In the context of the present invention, the term "seedless fruit" or "fruit comprising substantially no seed" is preferably understood to describe a fruit comprising in average no more than 5% of the viable seeds of a normal fruit, e.g. no more than 4%, 3%, 2.5%, 2%, 1.5%, 1%, or 0.5% of the viable seeds of a normal fruit.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids or nucleic acids) are referred to.

Plants and Methods of the Invention

The present invention provides a plant of the family Solanaceae comprising in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 70% sequence identity to SEQ ID NO:1.

The inventors surprisingly found that normal protein function of the wild type SSPER-1 protein in plants of the family Solanaceae is essential for the development of mature and/or viable seeds upon pollination. It was further surprisingly found that a mutant allele of the wild type SSPER-1 gene causes stenospermocarpic fruit formation when present in homozygous form. The mutant allele according to the present invention preferably represents a variant of a wild type gene designated herein as SSPER-1 which stands for stenospermocarpy pepper 1. It was further surprisingly found that the seedless fruits that can be produced by the plants according to the present invention have a normal shape and size. Particularly, no negative effect in the plants of the present invention producing seedless fruits were observed on with respect to the number of fruits, fruit size and pericarp thickness. This provides a significant improvement over the prior art. For instance, the currently available seedless peppers, which all are based on parthenocarpy, are characterized in that fruit size and/or fruit shape is altered when compared to their isogenic non-parthenocarpic counterparts and/or when compared to the normally fertilized non-seedless counterparts in the event of a facultative parthenocarpic trait.

Accordingly, the present invention provides a plant of the family Solanaceae comprising in its genome at least one copy of a mutant allele of the wild type SSPER-1 gene, wherein said mutant allele causes stenospermocarpic fruit formation when present in homozygous form. The wild type SSPER-1 gene encodes a protein comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO: 1, (as determined using methods discloses elsewhere herein).

In one embodiment, the mutant allele of the of the wild type SSPER-1 gene leads to a disruption of the normal (wild type) protein function of the protein encoded by SSPER-1 gene. The mutant allele as described herein thus may result in reduced expression or no expression of the wild type SSPER-1 gene. The mutant allele as described herein may also encode a protein having a decreased function or loss-of-function when compared to the wild type protein. Thus, the mutant allele that causes stenospermocarpic fruit formation when present in homozygous form may be associated with a reduced expression or even a loss of expression of an otherwise functional SSPER-1 gene product. In a non-limiting example, such a reduced expression or loss of expression may be the result of one or more mutations in a regulatory region of the SSPER-1 gene, e.g. in a promoter sequence of the SSPER-1 gene. In a further non-limiting example, such a reduced expression or loss of expression may be the result of one or more mutations in a transcription factor that is required for normal (wild type) expression of the SSPER-1 gene product (e.g. a functional variant of the wild type SSPER-1 protein). In a further non-limiting example, such a reduced expression or loss of expression may be the result of posttranscriptional gene silencing or RNAi. Means and methods to determine the expression level of a given gene are well known in the art including, but not limited to, quantitative reverse transcription polymerase chain reaction (quantitative RT-PCR) for the detection and quantification of a specific mRNA and enzyme-linked immunosorbent assay (ELISA) for the detection and quantification of a specific protein. The mutant allele that causes stenospermocarpic fruit formation when present in homozygous form may be associated with the expression of a protein having a decreased function or loss-of-function when compared to the wild type protein (e.g. a non-functional variant of the wild type SSPER-1 protein). In a non-limiting example, such a decreased function or loss-of-function may be the result of a mutation in the coding region of the SSPER-1 gene, resulting e.g. in one or more amino acids being replaced (e.g. through a frame-shift mutation or due to a missense mutation), inserted or deleted compared to the wild type protein. Means and methods to determine protein function are well known in the art including, but not limited to phenotypic testing assays for normal protein function (e.g. the detection of normal formation of mature and/or viable seeds in the fruit), bioassays capable of quantification of enzymatic activity and in silico prediction of amino acid changes that affect protein function, as further described herein above.

In one embodiment of the invention therefore concerns plant cells or plants of the family Solanaceae, especially species of the genus *Capsicum* or *Solanum*, comprising a mutant allele of a SSPER-1 protein-encoding gene characterized in that the mutant ssper-1 allele comprises or effects one or more of the mutations selected from the group consisting of:

(a) a deletion, truncation, insertion, point mutation, nonsense mutation, missense or non-synonymous mutation, splice-site mutation, frame shift mutation in the genomic sequence;
(b) a mutation in one or more regulatory sequences;
(c) a deletion, truncation, insertion, point mutation, nonsense mutation, missense or non-synonymous mutation, splice-site mutation, frame shift mutation in the coding sequence;
(d) a deletion, truncation, insertion, point mutation, nonsense mutation, missense or non-synonymous mutation, splice-site mutation, frame shift mutation in the pre-mRNA or mRNA; and/or
(e) a deletion, truncation, insertion or replacement of one or more amino acids in the SSPER-1 protein.

The above mutant allele results in decreased activity of the mutant SSPER-1 protein compared to the wild type SSPER-1 protein in the respective species. The decreased activity is due to a knock-out of expression of the SSPER-1 gene, a knock-down of expression of the gene, a loss of function of the encoded mutant SSPER-1 protein or a decrease of function of the mutant SSPER-1 protein.

In one embodiment, the present invention provides a plant comprising a mutant allele of the wild type SSPER-1 gene, wherein the mutant allele as described herein encodes a protein that is truncated when compared to the wild type protein. In one embodiment, the truncated ssper-1 protein comprises at the most amino acid residues 1-500 of SEQ ID NO:1 or a fragment thereof, which in the context of the present invention means that the truncated protein comprises at the most amino acid residues 1-500 of SEQ ID NO:1 (i.e. amino acid residues starting at, and including, amino acid 1 and ending at the most at, and including, amino acid 500 of SEQ ID NO:1) or any fragment in between said amino acid residues 1-500 of SEQ ID NO:1. For instance, the truncated protein of the present invention comprises at the most amino acid residues 1-400 of SEQ ID NO:1 or a fragment thereof, at the most amino acid residues 1-300 of SEQ ID NO:1 or a fragment thereof or at the most amino acid residues 1-200 of SEQ ID NO:1 or a fragment thereof. In one embodiment, the truncated ssper-1 protein of the present invention comprises the homeobox domain. In a further embodiment, the truncated ssper-1 protein of the present invention comprises amino acid residues 118-175 of SEQ ID NO:1 (i.e. amino acid residues starting at, and including, amino acid 118 and ending at, and including, amino acid 171 of SEQ ID NO:1). In one embodiment, the mutant ssper-1 allele in the species *Capsicum annuum* is the mutant ssper-1 cDNA (mRNA) sequence depicted in SEQ ID NO:4. In one embodiment, the mutant ssper-1 allele in the species *Capsicum annuum* encodes the mutant ssper-1 protein depicted in SEQ ID NO:3.

The plant of the present invention is a plant of the plant family Solanaceae. In one embodiment, the present invention provides a plant of the plant genus *Capsicum* comprising in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 70% amino acid sequence identity to SEQ ID NO:1. In said plant of the genus *Capsicum*, the wild type SSPER-1 gene encodes a protein comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO: 1, (as determined using methods discloses elsewhere herein). In one embodiment, the present invention provides a plant that is a *Capsicum annuum* plant, a *Capsicum chinense* plant, a *Capsicum baccatum* plant, a *Solanum melongena* plant, a *Solanum* pennellii plant or a *Solanum lycopersicum* plant. In said *Capsicum annuum* plant, the wild type SSPER-1 gene encodes a protein comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO: 1. In said *Capsicum chinense* plant, the wild type SSPER-1 gene encodes a protein comprising at least 70% amino acid sequence identity to SEQ ID NO:5, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO: 5. In said *Capsicum baccatum* plant, the wild type SSPER-1 gene encodes a protein comprising at least 70% amino acid sequence identity to SEQ ID NO:7, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO: 7. In said *Solanum melongena* plant, the wild type SSPER-1 gene encodes a protein comprising at least 70% amino acid sequence identity to SEQ ID NO:9, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:9. In said *Solanum lycopersicum* plant, the wild type SSPER-1 gene encodes a protein comprising at least 70% amino acid sequence identity to SEQ ID NO:13, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:13.

The plant according to the present invention comprises at least one copy of the mutant allele as provided herewith. Such a plant thus may be heterozygous for the mutant allele of the present invention. Such a heterozygous plant comprises (at least) one copy of the wild type allele and (at least) one copy of the mutant allele of the present invention. Such a heterozygous plant may show a phenotype wherein the produced fruits partially comprise mature and/or viable seeds (i.e. a reduced number of mature and/or viable seeds when compared to comparable fruits of a homozygous wild type plant). The present invention thus is also directed to plants comprising the mutant ssper-1 allele of the present invention in heterozygous form. Such heterozygous plants can also be advantageously used for breeding to generate offspring that is homozygous for the mutant ssper-1 allele as further described herein below. In one embodiment, the present invention provides a plant that is homozygous for the mutant allele of the present invention. Such a plant is inter alia characterized in that it is capable of stenospermocarpic fruit formation, as further described herein below.

The plants of the present invention may be any plant of the family Solanaceae as described herein, comprising in its genome at least one copy of a mutant allele of the wild type SSPER-1 gene. In one embodiment, the present invention provides a plant as described herein that further is an inbred plant, a dihaploid plant or a hybrid plant. In one aspect, accordingly, the present invention provides that the plant of the present invention is an inbred plant. Such an inbred plant is highly homozygous, for instance by repeated selfing crossing steps. Such an inbred plant may be very useful as a parental plant for the production of F1 hybrid seed. In one aspect, the disclosure provides for haploid plants and/or dihaploid (double haploid) plants of plant of the invention are encompassed herein, which comprise the mutant ssper-1 allele as described herein. Haploid and dihaploid plants can for example be produced by anther or microspore culture and regeneration into a whole plant. For dihaploid production chromosome doubling may be induced using known methods, such as colchicine treatment or the like. So, in one aspect a solanaceous plant is provided, comprising the stenospermocarpic fruit formation phenotype as described, wherein the plant is a dihaploid plant. The present invention further provides hybrid plants, which may have advantages such as improved uniformity, vitality and/or disease tolerance.

The plants provided by the present invention may be used to produce fruits. The present invention thus provides the use of a plant of the family Solanaceae as provided herein as a crop for consumption. Particularly the fruits produced by the plants of the present invention can be advantageously used as a crop for consumption since these fruits comprise significantly less or even substantially no viable and/or mature seeds.

The plants provided by the present invention may be used to produce propagation material. Such propagation material comprises propagation material suitable for and/or resulting from sexual reproduction, such as pollen and seeds. Such propagation material comprises propagation material suitable for and/or resulting from asexual or vegetative reproduction including, but not limited to cuttings, grafts, tubers, cell culture and tissue culture. The present invention thus further provides the use of a plant of the family Solanaceae as provided herein as a source of propagation material.

Seeds

The present invention provides seed from which any plant according to the invention can be grown. Furthermore, the invention provides a plurality of such seed. A seed of the invention can be distinguished from other seeds due to the presence of the mutant allele of the wild type SSPER-1 gene as described herein, either phenotypically (based on plants having the stenospermocarpic fruit formation phenotype) and/or using molecular methods to detect the mutant allele in the cells or tissues, such as molecular genotyping methods to detect the mutant allele of the present invention or sequencing. Seeds include for example seeds produced on a plant of the invention which is heterozygous for the mutant allele after self-pollination and optionally selection of those seeds which comprise one or two copies of the mutant allele (e.g. by nondestructive seed sampling methods and analysis of the presence of the ssper-1 allele), or seed produced after cross-pollination, e.g. pollination of a plant of the invention with pollen from another solanaceous plant or pollination of another solanaceous plant with pollen of a plant of the invention.

Particularly, the present invention provides pollen or seed produced by the plant according to the present invention, or seed from which a plant of the invention can be grown, wherein said plant is a plant of the family Solanaceae comprising in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 70% sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1.

Particularly, the present invention provides pollen or seed produced by the plant according to the present invention, or seed from which a plant of the invention can be grown, wherein the pollen or seed comprises the mutant allele of the wild type SSPER-1 gene as defined as defined herein that is capable of causing stenospermocarpic fruit formation when present in homozygous form. Particularly, the present invention provides seed from which the plant of the present invention can be grown.

In one aspect seeds are produced by crossing a first Solanaceae plant which is heterozygous for the mutant ssper-1 allele and a second Solanaceae plant which is homozygous for the wild type SSPER-1 allele, whereby about 50% of the seeds harvested from said cross are homozygous for the mutant ssper-1 allele and about 50% of the seeds harvested are heterozygous for the mutant ssper-1 allele. In this method the seeds homozygous for the mutant ssper-1 allele are optionally selected, using e.g. non-destructive seed DNA sampling, or seedlings homozygous for the mutant SSPER-1 allele are selected, using e.g. DNA analysis of cotyledon or leaf samples. Thus, in one aspect a method for selecting seeds or seedlings which are homozygous for the mutant ssper-1 allele is provided herein. This method involves providing a plurality of seeds which segregate for the mutant ssper-1 allele and either a) using non-destructive seed sampling and analysis of the presence or absence of the mutant ssper-1 allele in the seeds to select those seeds which comprise two copies of the mutant ssper-1 allele, and/or b) germinating the seeds and analyzing cotyledon or leaf samples of the seedlings for the presence or absence of the mutant ssper-1 allele and selecting those seedlings which comprise two copies of the mutant ssper-1 allele. The plants grown from the selected seeds or the selected seedlings will produce seedless fruits. They can therefore be sold to the customers. A plurality of selected seeds or seedlings, all of which are homozygous for the mutant ssper-1 allele, are an embodiment of the invention.

The present invention further provides seeds obtained from the methods of producing plants as described herein.

In one aspect, a plurality of seed is packaged into a container (e.g. a bag, a carton, a can etc.). Containers may be any size. The seeds may be pelleted prior to packing (to form pills or pellets) and/or treated with various compounds, including seed coatings.

Plant Parts and Vegetative Reproductions

In a further aspect a plant part, obtained from (obtainable from) a plant of the invention is provided herein, and a container or a package comprising said plant part.

Particularly, the present invention provides a part from the plant of the present invention, wherein the part comprises in its genome at least one copy of the mutant ssper-1 allele as described herein, preferably wherein the part is selected from the group consisting of a fruit, leaf, anther, pistil, stem, petiole, root, ovule, pollen, protoplast, tissue, seed, flower, cotyledon, hypocotyl, embryo and cell. Accordingly, the present invention provides a part of the plant according to the present invention, wherein said plant part is a leaf, anther, pistil, stem, petiole, root, ovule, pollen, protoplast, tissue, seed, flower, cotyledon, hypocotyl, embryo or cell and wherein said part comprises in its genome at least one copy of the mutant ssper-1 allele as described herein. The part of the plant according to the present invention comprising in its genome at least one copy of the mutant ssper-1 allele preferably is homozygous for the mutant ssper-1 allele as described herein. The various stages of development of aforementioned plant parts are comprised in the invention.

Particularly, fruit produced by the plant of the present invention is provided. Plants according to the present invention may be heterozygous for the mutant allele of the SSPER-1 gene. The fruits produced by such heterozygous plants may already show a phenotype that can be distinguished from fruits produced by a comparable plant that is homozygous for a wild type allele of the SSPER-1 gene. For instance, a heterozygous plant may produce fruits that comprise a reduced number of mature and/or viable seeds when compared to comparable fruits of a homozygous wild type plant. Preferably, the fruit is homozygous for the mutant allele of the SSPER-1 gene and is seedless. The present invention, accordingly specifically provides seedless pepper fruit in the event the plant is a *Capsicum annuum* plant comprising the mutant ssper-1 allele of the present invention in homozygous form, a *Capsicum chinense* plant or a *Capsicum baccatum* plant, seedless eggplant fruit in the event the plant is a *Solanum melongena* plant comprising the mutant ssper-1 allele of the present invention in homozygous form and seedless tomato fruit in the event the plant is a *Solanum lycopersicum* plant comprising the mutant ssper-1 allele of the present invention in homozygous form. The present invention further provides a (processed) food product comprising the fruit produced by the plant as described herein. Preferably, the fruit comprised in said (processed) food product is produced by a plant that is homozygous for the mutant allele of the SSPER-1 gene and accordingly is seedless.

Preferably, the fruit homozygous for the mutant allele of the SSPER-1 gene has the same shape and/or size when compared to the fruits of genetically identical plants comprising two copies of a wild type allele of the SSPER-1 gene. It was surprisingly found in the context of the present invention that the seedless fruits that can be produced by the plants according to the present invention have a normal shape and size. The present invention therefore for the first time provides seedless fruit produced by a plant of the family Solanaceae having the same shape and/or size when compared to the fruits of genetically identical wild type plants (i.e. plants comprising two copies of a wild type allele of the SSPER-1 gene).

The present invention further provides a part of the plant according to the present invention, wherein said plant part may be a leaf, anther, pistil, stem, petiole, root, ovule, pollen, protoplast, tissue, seed, flower, cotyledon, hypocotyl, embryo or cell.

In a further aspect, the plant part is a plant cell. In still a further aspect, the plant part is a non-regenerable cell or a regenerable cell. In another aspect the plant cell is a somatic cell.

A non-regenerable cell is a cell which cannot be regenerated into a whole plant through in vitro culture. The non-regenerable cell may be in a plant or plant part (e.g. leaves) of the invention. The non-regenerable cell may be a cell in a seed, or in the seedcoat of said seed. Mature plant organs, including a mature leaf, a mature stem or a mature root, contain at least one non-regenerable cell.

In a further aspect the plant cell is a reproductive cell, such as an ovule or a cell which is part of a pollen. In an aspect, the pollen cell is the vegetative (non-reproductive) cell, or the sperm cell (Tiezzi, Electron Microsc. Review, 1991). Such a reproductive cell is haploid. When it is regenerated into whole a plant, it comprises the haploid genome of the starting plant. If chromosome doubling occurs (e.g. through chemical treatment), a double haploid plant can be regenerated. In one aspect the plant of the invention comprising the mutant ssper-1 allele is a haploid or a double haploid solanaceous plant.

Moreover, there is provided an in vitro cell culture or tissue culture of the solanaceous plant of the invention in which the cell- or tissue culture is derived from a plant part described above, such as, for example and without limitation, a leaf, a pollen, an embryo, cotyledon, hypocotyls, callus, a root, a root tip, an anther, a flower, a seed or a stem, or a part of any of them, or a meristematic cell, a somatic cell, or a reproductive cell.

The present invention further provides a vegetatively propagated plant, wherein said plant is propagated from a plant part according to the present invention.

Further, isolated cells, in vitro cell cultures and tissue cultures, protoplast cultures, plant parts, harvested material (e.g. harvested pepper fruits), pollen, ovaries, flowers, seeds, stamen, flower parts, etc. comprising in each cell at least one copy of the mutant ssper-1 allele of the present invention are provided. Thus, when said cells or tissues are regenerated or grown into a whole solanaceous plant, the plant comprises the mutant allele capable of causing stenospermocarpic fruit formation when present in homozygous form.

Thus, also an in vitro cell culture and/or tissue culture of cells or tissues of plants of the invention is provided. The cell or tissue culture can be treated with shooting and/or rooting media to regenerate a solanaceous plant.

Also vegetative or clonal propagation of plants according to the invention is encompassed herein. Many different vegetative propagation techniques exist. Cuttings (nodes, shoot tips, stems, etc.) can for example be used for in vitro culture as described above. Also other vegetative propagation techniques exist and can be sued, such as grafting, or air layering. In air layering a piece of stem is allowed to develop roots while it is still attached to the parent plant and once enough roots have developed the clonal plant is separated from the parent.

Thus, in one aspect a method is provided comprising:

(a) obtaining a part of a plant of the invention (e.g. cells or tissues, e.g. cuttings),
(b) vegetatively propagating said plant part to generate an identical plant from the plant part.

Thus, also the use of vegetative plant parts of plants of the invention for clonal/vegetative propagation is an embodiment of the invention. In one aspect a method is provided for vegetatively reproducing a solanaceous plant of the invention (preferably *C. annuum*) comprising two copies of a mutant ssper-1 allele is provided. Also a vegetatively produced plant comprising two copies if a mutant ssper-1 allele is provided.

In another aspect a plant of the invention, comprising two copies of the mutant ssper-1 allele according to the invention, is propagated by somatic embryogenesis techniques.

Also provided is a solanaceous plant regenerated from any of the above-described plant parts, or regenerated from the above-described cell or tissue cultures, said regenerated plant comprising in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1. This plant can also be referred to as a vegetative propagation of plants of the invention. Preferably, the regenerated plant is homozygous for the mutant ssper-1 allele of the present invention and thus is capable of stenospermocarpic fruit formation.

The invention also relates to a food or feed product comprising or consisting of a plant part described herein. The food or feed product may be fresh or processed, e.g., canned, steamed, boiled, fried, blanched and/or frozen etc. Examples are sandwiches, salads, juices, sauces, fruit pastes, ketchup or other food products comprising a fruit or a part of a fruit of a plant of the invention.

The present invention further provides the use of a nucleic acid encoding the SSPER-1 protein for the identification of a plant of the family Solanaceae capable of stenospermocarpic fruit formation, wherein said SSPER-1 protein comprises at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1. The present invention further provides the use of a nucleic acid sequence encoding the SSPER-1 protein for the identification of a plant of the family Solanaceae capable of stenospermocarpic fruit formation, wherein said SSPER-1 protein comprises at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1. For instance, the nucleic acid sequence encoding the SSPER-1 protein of the present invention can be used to design a genetic marker useful for the identification and/or selection of a plant of the family Solanaceae capable of stenospermocarpic fruit formation, wherein said SSPER-1 protein comprises at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1.

The present invention further provides the use of a nucleic acid sequence encoding the SSPER-1 protein for breeding plants of the family Solanaceae capable of stenospermocarpic fruit formation, wherein said SSPER-1 protein comprises at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1. For instance, the nucleic acid sequence encoding the SSPER-1 protein of the present invention can be used to determine whether a plant is suitable as a parental plant in breeding, e.g. to produce seed from which a plant of the family Solanaceae capable of stenospermocarpic fruit formation can be grown.

Plants and Progeny

In another embodiment, plants and parts of solanaceous plants of the invention, and progeny of solanaceous plant of the invention are provided, e.g., grown from seeds, produced by sexual or vegetative reproduction, regenerated from the above-described plant parts, or regenerated from cell or tissue culture, in which the reproduced (seed propagated or vegetatively propagated) plant comprises at least one copy of the mutant ssper-1 allele of the present invention.

The present invention further provides a plant of the family Solanaceae grown from the seed as described herein. The present invention thus provides a solanaceous plant grown from seeds obtained from the method for producing a solanaceous plant as described herein.

Furthermore, the invention provides progeny comprising or retaining the stenospermocarpic fruit formation phenotype (conferred by the mutant ssper-1 allele), such as progeny obtained by, e.g., selfing one or more times and/or cross-pollinating a plant of the invention with another solanaceous plant of a different variety or breeding line of the same plant species (or of a plant species that can be crossed with the solanaceous plant of the present invention), or with a solanaceous plant of the invention one or more times. In particular, the invention provides progeny homozygous for the mutant ssper-1 allele capable of forming seedless fruit. In one aspect the invention relates to for a progeny plant comprising the mutant ssper-1 allele, such as a progeny plant that is produced from a solanaceous plant comprising the mutant ssper-1 allele by one or more methods selected from the group consisting of: selfing, crossing, mutation, double haploid production or transformation. Mutation preferable are human induced mutations or somaclonal mutations. In one embodiment, plants or seeds of the invention may also be mutated (by e.g. irradiation, chemical mutagenesis, heat treatment, TILLING, etc.) and/or mutated seeds or plants may be selected (e.g. somaclonal variants, etc.) in order to change one or more characteristics of the plants. Similarly, plants of the invention may be transformed and regenerated, whereby one or more chimeric genes are introduced into the plants. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into the plants, or progeny thereof, by transforming a plant of the invention or progeny thereof with a transgene that confers the desired trait, wherein the transformed plant retains the mutant ssper-1 allele and, when the mutant ssper-1 allele is comprised in homozygous form, the stenospermocarpic fruit formation phenotype conferred by it and contains the desired trait.

In another embodiment the invention relates to a method for producing seed, comprising crossing a plant of the invention with itself or a different plant and harvesting the resulting seed. In a further embodiment the invention relates to seed produced according to this method and/or a plant produced by growing such seed. Thus, a plant of the invention may be used as male and/or female parent, in the production of seeds, whereby the plants grown from said seeds comprise the mutant ssper-1 allele as provided herewith. The present invention thus further provides a plant grown from the seed of the present invention.

Thus, in one aspect progeny of a solanaceous plant of the invention are provided, wherein the progeny plant is produced by selfing, crossing, mutation, double haploid production or transformation and preferably wherein the progeny retain the mutant ssper-1 allele.

The present invention further provides a method of producing stenospermocarpic fruit, said method comprising growing a plant according to the present invention and harvesting the fruits produced by said plants. Preferably, the plant producing the stenospermocarpic fruit according to the method of the present invention is homozygous for the mutant ssper-1 allele as described herein and accordingly is seedless.

The present invention further provides a method of identifying and/or selecting a plant or plant part of the family Solanaceae comprising a mutant allele of the SSPER-1 gene comprising determining whether the plant or plant part comprises a mutant allele of an SSPER-1 gene, wherein said mutant allele results in reduced expression or no expression of the SSPER-1 gene or wherein the mutant allele encodes a protein having a decreased function or loss-of function when compared to the wild type protein and optionally selecting a plant or plant part comprising at least one copy of a mutant allele of the SSPER-1 gene wherein said mutant allele causes stenospermocarpic fruit formation when present in homozygous form, wherein the wild type SSPER-1 gene encodes a protein comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1.

The method comprises screening at the DNA, RNA (or cDNA) or protein level using known methods, in order to detect the presence of the mutant allele according to the present invention. There are many methods to detect the presence of a mutant allele of a gene.

For example, if there is a single nucleotide difference (single nucleotide polymorphism, SNP) between the wild type and the mutant allele, a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p097-1098 for KASP-assay method.

Equally other genotyping assays can be used. For example, a TaqMan SNP genotyping assay, a High Resolution Melting (HRM) assay, SNP– genotyping arrays (e.g. Fluidigm, Illumine, etc.) or DNA sequencing may equally be used.

Molecular markers may also be used to aid in the identification of the plants (or plant parts or nucleic acids obtained therefrom) containing the mutant ssper-1 allele. For example, one can develop one or more suitable molecular markers which are closely genetically (and preferably also physically) linked to the mutant ssper-1 allele. This can be done by crossing a solanaceous plant according to the present invention (preferably capable of stenospermocarpic fruit formation) with a wild type plant and developing a segregating population (e.g. F2 or backcross population) from that cross. The segregating population can then be phenotyped for stenospermocarpic fruit formation and genotyped using e.g. molecular markers such as SNPs (Single Nucleotide Polymorphisms), AFLPs (Amplified Fragment Length Polymorphisms; see, e.g., EP 534 858), or others, and by software analysis molecular markers which co-segregate with the stenospermocarpic fruit formation trait in the segregating population can be identified and their order and genetic distance (centimorgan distance, cM) to the SSPER-1 gene (or locus) can be identified. Molecular markers which are closely linked to SSPER-1 locus, e.g. markers at a 5 cM distance or less, can then be used in detecting and/or selecting plants (e.g. plants of the invention or progeny of a plant of the invention) or plant parts comprising or retaining the introgression fragment comprising the mutant ssper-1 allele. Such closely linked molecular markers can replace phenotypic selection (or be used in addition to phenotypic selection) in breeding programs, i.e. in Marker Assisted Selection (MAS). Preferably, linked markers are used in MAS. More preferably, flanking markers are used in MAS, i.e. one marker on either side of the locus of the mutant ssper-1 allele.

Preferably, the plant or plant part is subjected to a mutation inducing step prior to determining whether the plant or plant part comprises a mutant allele of an SSPER-1 gene. Said mutation inducing step may comprise contacting said plant or plant part with a mutagen. Said mutation inducing step may also encompass targeted mutagenesis techniques such as CRISPR-Cas. Preferably, the plant that is contacted with the mutagen comprises a wild type SSPER-1 allele in homozygous form. The mutation inducing step subsequently causes a mutation in the wild type SSPER-1 allele to provide a mutant ssper-1 allele that is capable of causing stenospermocarpic fruit formation. Also transgenic plants can be made using the mutant ssper-1 nucleotide sequences of the invention using known plant transformation and regeneration techniques in the art. An "elite event" can be selected, which is a transformation event having the chimeric gene (comprising a promoter operably linked to a nucleotide sequence encoding a loss-of-function ssper-1 protein or reduced-function ssper-1 protein) inserted in a particular location in the genome, which results in good expression of the desired phenotype. Also transgenic plants can be made comprising a construct which reduces or abolishes the expression of the endogenous (wild type) ssper-1 gene, such as an RNAi construct.

The present invention accordingly provides a method of producing a solanaceous plant of the invention comprising the steps of:

(a) obtaining plant material from a plant of the family Solanaceae;

(b) treating said plant material with a mutagen to create mutagenized plant material;

(c) analyzing said mutagenized plant material to identify a plant having at least one mutation in SSPER-1 gene, wherein the wild type SSPER-1 gene encodes a protein comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1.

TILLING (Targeting Induced Local Lesions IN Genomes) is a general reverse genetics technique that uses traditional chemical mutagenesis methods to create libraries of mutagenized individuals that are later subjected to high throughput screens for the discovery of mutations. TILLING combines chemical mutagenesis with mutation screens of pooled PCR products, resulting in the isolation of missense and non-sense mutant alleles of the targeted genes. Thus, TILLING uses traditional chemical mutagenesis (e.g. EMS or MNU mutagenesis or mutagenesis by generating reactive oxygen species) or other mutagenesis methods (e.g. by radiation mutagenesis using e.g. UV radiation or ion beam radiation) followed by high-throughput screening for mutations in specific target genes, such as the SSPER-1 gene according to the invention. 51 nucleases, such as CEL1 or ENDO1, are used to cleave heteroduplexes of mutant and wildtype target DNA and detection of cleavage products using e.g. electrophoresis such as a LI-COR gel analyzer system, see e.g. Henikoff et al. Plant Physiology 2004, 135: 630-636. TILLING has been applied in many plant species, including solanaceous plants such as tomato. (see http://tilling.ucdavis.edu/index.php/Tomato_Tilling), rice (Till et al. 2007, BMC Plant Biol 7: 19), *Arabidopsis* (Till et al. 2006, Methods Mol Biol 323: 127-35), *Brassica*, maize (Till et al. 2004, BMC Plant Biol 4: 12), etc. Also EcoTILLING, whereby mutants in natural populations are detected, has been widely used, see Till et al. 2006 (Nat Protoc 1: 2465-77) and Comai et al. 2004 (Plant J 37: 778-86).

In one embodiment of the invention (cDNA or genomic) nucleic acid sequences encoding such mutant SSPER-1 proteins comprise one or more non-sense and/or missense mutations, e.g. transitions (replacement of purine with another purine (A↔G) or pyrimidine with another pyrimidine (C↔T)) or transversions (replacement of purine with pyrimidine, or vice versa (C/T↔A/G). In one embodiment the non-sense and/or missense mutation(s) is/are in the nucleotide sequence encoding any of the SSPER-1 exons, or an essentially similar domain of a variant SSPER-1 protein, i.e. in a domain comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1.

In one embodiment a SSPER-1 nucleotide sequence comprising one or more non-sense and/or missense mutations in one of the exon-encoding sequence are provided, as well as a plant comprising such a mutant allele resulting in a plant capable of stenospermocarpic fruit formation when said mutant allele is present in homozygous form.

In one aspect, accordingly, the plant or plant part is identified and/or selected from a TILLING population that was obtained by subjecting plants or plant parts to a mutagen. Thus, in one aspect a method for producing a is provided comprising the steps of:

(a) providing a TILLING population of a plant species of the family Solanaceae, (b) screening said TILLING population for mutants in the SSPER-1 gene, wherein the wild type SSPER-1 gene encodes a protein comprising at least 70% amino acid sequence identity to SEQ ID NO:1, e.g. 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.3%, 98.7%, 99.0%, or 99.3% or more preferably 99.7% sequence identity to SEQ ID NO:1, and (c) selecting from the mutant plants of (b) those plants (or progeny of those plants) which are capable of stenospermocarpic fruit formation.

Mutant plants (M1) are preferably selfed one or more times to generate for example M2 populations or preferably M3 or M4 populations for phenotyping. In M2 populations the mutant allele is present in a ratio of 1 (homozygous for mutant allele):2 (heterozygous for mutant allele):1 (homozygous for wild type allele).

The present invention further provides a method of producing a plant of the family Solanaceae comprising in its genome at least one copy of a mutant allele of the SSPER-1 gene as defined herein, wherein said mutant allele causes stenospermocarpic fruit formation when present in homozygous form, said method comprising the step(s) of:

(i) crossing a first Solanaceae plant and a second Solanaceae plant, wherein the first Solanaceae plant is the plant according to the present invention;

(ii) optionally harvesting seed from the crossing of (i) and selecting seed comprising in its genome at least one copy of a mutant allele of the SSPER-1 gene as described herein. Said method for producing a plant of the family Solanaceae comprising in its genome at least one copy of a mutant allele of the SSPER-1 gene may further comprise a process step comprising determining whether the plant comprises a mutant allele of an SSPER-1 gene as described herein.

In one aspect the first Solanaceae plant is heterozygous for the mutant SSPER-1 allele and the second Solanaceae plant is homozygous for the wild type SSPER-1 allele, whereby a proportion of the seeds harvested from said cross are homozygous for the mutant SSPER-1 allele and the remaining seeds are heterozygous for the mutant SSPER-1 allele. In this method, seeds homozygous for the mutant SSPER-1 allele optionally are subsequently selected, using e.g. non-destructive seed DNA sampling, or seedlings homozygous for the mutant SSPER-1 allele are selected, using e.g. DNA analysis of cotyledon or leaf samples.

Preferably, both the first Solanaceae plant and the second Solanaceae plant in step (i) of the method of producing the solanaceous plant as provided herein are plants according to the present invention.

The present invention further provides a plant grown from seeds obtained by the method of identifying and/or selecting a plant or plant part of the family Solanaceae comprising a mutant allele of the SSPER-1 gene as described herein. The present invention further provides a plant grown from seeds obtained by the method of producing a plant of the family Solanaceae comprising in its genome at least one copy of a mutant allele of the SSPER-1 gene as defined herein.

The present invention further provides a method for the production of a plant of the family Solanaceae capable of stenospermocarpic fruit formation by growing a seed according to the present invention, wherein said plant is homozygous for the mutant allele.

In one aspect, the stenospermocarpic fruit formation trait is caused by a mutation in the ssper-1 allele or orthologous allele or homologous allele. Thus in one aspect a specific mutant ssper-1 allele is provided. Mutagenesis techniques such as chemical or UV mutagenesis can be used, or targeted mutagenesis techniques such as CRISPR-Cas can be used to induce mutations in a wild type SSPER-1 gene which confer stenospermocarpic fruit formation trait of the present invention. In one aspect plants, plant parts and cells according to the invention are not exclusively obtained by means of an essentially biological process as defined by Rule 28(2) EPC.

EXAMPLES

Example 1

Random Mutagenesis Followed by Phenotypical Evaluation.

Mutations can be induced by ionizing radiation producing DNA strand breaks and oxidative DNA lesions by generating reactive oxygen species (ROS). One of the oxidation product induced by ROS is 8-oxo-7-hydrodeoxyguanosine (8-oxo-dG) that can induce a G/C-to-T/A transversion in the DNA. Mutations can be generated in pollen by harvesting flower buds and irradiate them at room temperature with various doses of, e.g. 100 Gy, γ-rays from a $^{60}$Co source (Akbudak et al. (2009) New Zealand Journal of Crop and Horticultural Science 37: 361-367). The irradiated pollen containing mutations varying from single base substitutions or deletions to large deletions spanning several mega bases can be used to cross untreated plants (Ryouhei Morita, et al. (2009) Genes Genet Syst. 84:361-70). Seeds from the cross (F1) can be sowed again and viable seeds will grow out to generate plants with each its own set of specific mutations. Seeds from the F1 can be collected per plant and grown in turn to be phenotyped. The mutations segregate in the F2 families and their phenotypic effects can be evaluated.

Example 2

Random Mutagenesis Followed by Reverse Screening from TILLING Mutant Population.

A highly homozygous inbred line used in commercial pepper breeding can be used for mutagenesis treatment with the following protocol. After seed imbibition on damp Whatman® paper for 24 h, −20,000 seeds, divided in 8 batches of 2500 respectively, is soaked in 100 ml of ultra-pure water and ethyl methanesulfonate (EMS) at a concentration of 1% in conical flasks. The flasks are gently shaken for 16 h at room temperature. Finally, EMS is rinsed out under flowing water. Following EMS treatment, seeds are directly sown in the greenhouse. Out of the seeds that germinate, a sufficient number of plantlets are transplanted in the field. From these plantlets, at least one fruit is harvested from the surviving and plant bearing plants. For instance, from each remaining M1 mutant plant one fruits is harvested and its seeds isolated. From the obtained population, named M2 population, specific families may be excluded from the population due to low seed set.

DNA is extracted from a pool of 10 seeds originating from each M2 seed lot. Per mutant line, seeds are pooled in a Micronic® deepwell tube; world wide web at micronic.com from a 96 deep-well plate, 2 stainless balls are added to each tube. The tubes and seeds are frozen in liquid nitrogen for 1 minute and seeds are immediately ground to a fine powder in a Deepwell shaker (Vaskon 96 grinder, Belgium; world wide web at vaskon.com) for 2 minutes at 16.8 Hz (80% of the maximum speed). 300 µl Agowa® Lysis buffer P from the AGOWA® Plant DNA Isolation Kit world wide web at agowa.de is added to the sample plate and the powder is suspended in solution by shaking 1 minute at 16.8 Hz in the Deepwell shaker. Plates are centrifuged for 10 minutes at 4000 rpm. 75 µl of the supernatant is pipetted out to a 96 Kingfisher plate using a Janus MDT® (Perkin Elmer, USA; world wide web at perkinelmer.com) platform (96 head). The following steps are performed using a Perkin Elmer Janus® liquid handler robot and a 96 Kingfisher® (Thermo labsystems, Finland; world wide web at thermo.com). The supernatant containing the DNA is diluted with binding buffer (150 pa) and magnetic beads (20 µl). Once DNA is bound to the beads, two successive washing steps are carried out (Wash buffer 1: Agowa wash buffer 1 1/3, ethanol 1/3, isopropanol 1/3; Wash buffer 2: 70% ethanol, 30% Agowa wash buffer 2) and finally eluted in elution buffer (100 µl MQ, 0.025 µl Tween).

Grinding 4 *C. annuum* seeds generally produces enough DNA to saturate the magnetic beads, thus highly homogenous and comparable DNA concentrations of all samples are obtained. Comparing with lambda DNA references, a concentration of 30 ng/µl for each sample is estimated. Two times diluted DNA was 4 fold flat pooled. 2 µl pooled DNA was used in multiplex PCRs for mutation detection analysis.

High Resolution Melt curve analysis (HRM) is proven to be sensitive and high-throughput methods in human and plant genetics. HRM is a non-enzymatic screening technique. During the PCR amplification dye (LCGreen+ dye, Idaho Technology Inc., UT, USA) molecules intercalate between each annealed base pair of the double stranded DNA molecule. When captured in the molecule, the dye emits fluorescence at 510 nm after excitation at 470 nm. A camera in a fluorescence detector (LightScanner, Idaho Technology Inc., UT, USA) records the fluorescence intensity while the DNA sample is progressively heated. At a temperature dependent on the sequence specific stability of the DNA helices, the double stranded PCR product starts to melt, releasing the dye. The release of dye results in decreased fluorescence that is recorded as a melting curve by the fluorescence detector. Pools containing a mutation form hetero duplexes in the post-PCR fragment mix. These are identified as differential melting temperature curves in comparison to homo duplexes.

Primers useful to amplify gene fragments for HRM are designed using a computer program (Primer3, http://primer3.sourceforge.net/). The length of the amplification product is limited between 200 and 400 base pairs. Quality of the primers is determined by a test PCR reaction that should yield a single product.

Polymerase Chain Reaction (PCR) to amplify gene fragments can be performed as follows. 10 ng of genomic DNA is mixed with 4 µl reaction buffer (5× Reaction Buffer), 2 µl 10×LC dye ((LCGreen+ dye, Idaho Technology Inc., UT, USA), 5 pmole of forward and reverse primers each, 4 nmole dNTPs (Life Technologies, NY, USA) and 1 unit DNA polymerase (Hot Start II DNA Polymerase) in a total volume of 10 µl. Reaction conditions were: 30 s 98° C., then 40 cycles of 10 s. 98° C., 15 s 60° C., 25 s of 72° C. and finally 60 s at 72° C.

The presence of a particular mutation in individual plants is confirmed by repeating the HRM analysis on DNA from the individual M2 seed lots of the identified corresponding DNA pool. When the presence of the mutation, based on the HRM profile, is confirmed in one of the four individual M2 family DNA samples, the PCR fragments are sequenced to identify the mutation in the gene.

Once the mutation is known the effect of such a mutation can be predicted, e.g. by using a computer program CODDLe (for Choosing codons to Optimize Discovery of Deleterious Lesions, http://www.proweb.org/coddle/) that identifies the region(s) of a user-selected gene and of its coding sequence where the anticipated point mutations are most likely to result in deleterious effects on the gene's function.

Seeds from M2 families that contain mutations with predicted effect on protein activity are sown for phenotypic analysis of the plants. Homozygous mutants are selected or obtained after selfing and subsequent selection. The effect of the mutation on the corresponding protein and phenotype of the plant is subsequently determined, for instance by using the methods as described herein below.

Example 3

Characterization of Seedless Pepper Plant According to the Present Invention.

The *C. annuum* plants of the various types to be tested (blocky, sweet pointed and Lamuyo) selected from segregating generations (F3 and F4) and corresponding control plants having the same genetic background except for being homozygous for the wild type SSPER-1 allele) were sown and grown under the same conditions until they are regularly producing mature fruits. The selected plants were multiplied with grafting method of vegetative propagation and established trial with four plants of two replicates in the autum winter cycle in Almeria, Spain. The growth conditions were: glasshouse, sufficient water supply, temperature: around 26° C./18° C. day/night with a photoperiod of about 14 h, light intensity: around 120 μmol*sec$^{-1}$*m$^{-2}$ μ[PAR], growth medium: soil (half turf and half pit). Subsequently, at least three mature fruits per plant were harvested and characterized directly after harvest for the following characteristics: average fruit length (cm), average fruit width (cm) and average fruit weight (g). The results of this characterization is provided in the following Table.

| | | Average Fruit dimension (cm) | | Average Fruit weight |
|---|---|---|---|---|
| Type | Generation | Length | Width | (g) |
| Blocky | Wild type elite line (control SSPER-1/SSPER-1) | 10.2 | 9.1 | 250 |
| | F3 (seedless ssper-1/ssper-1) | 10.1 | 9.2 | 245 |
| | F3 (seedless ssper-1/ssper-1) | 9.5 | 9.1 | 220 |
| Sweet | Wild type elite line (control SSPER-1/SSPER-1) | 19.7 | 4.2 | 117 |
| pointed | F4 (seedless ssper-1/ssper-1) | 17.6 | 5.8 | 133 |

-continued

| | | Average Fruit dimension (cm) | | Average Fruit weight |
|---|---|---|---|---|
| Type | Generation | Length | Width | (g) |
| | F3 (seedless ssper-1/ssper-1) | 16.3 | 4.9 | 100 |
| | F3 (seedless ssper-1/ssper-1) | 18.2 | 6.0 | 175 |
| Lamuyo | Wild type elite line (control SSPER-1/SSPER-1) | 15.1 | 9.2 | 317 |
| | F4 (seedless ssper-1/ssper-1) | 15.1 | 9.6 | 333 |
| | F3 (seedless ssper-1/ssper-1) | 14.0 | 8.2 | 200 |

Accordingly, it can be concluded that the seedless fruits that can be produced by the plants according to the present invention have a normal shape and size.

Example 4

Propagation of Seedless Pepper Plant of the Present Invention.

*C. annuum* plants producing seedless fruits as the result of said plants being homozygous for the mutant allele of the SSPER-1 gene according to the present invention (ssper-1/ssper-1) are multiplied by grafting and/or other conventional methods of vegetative propagation, such as cutting.

Alternatively, sib mating is used to propagate *C. annuum* plants producing seedless fruits by crossing a plant producing seedless fruits and which is homozygous for the mutant SSPER-1 allele (ssper-1/ssper-1) with a plant which is heterozygous for the mutant SSPER-1 allele (SSPER-1/ssper-1) of same family or lineage. The seeds produced by such a sib mating represents a population segregating for the seedless trait governed by the mutant SSPER-1 allele. The accordingly produced seeds that are homozygous for the mutant SSPER-1 allele (ssper-1/ssper-1), or the plants grown from such seeds, can be distinguished and/or separated from the also produced offspring that is heterozygous for the mutant SSPER-1 allele (SSPER-1/ssper-1) by using molecular genotyping methods as described herein

The invention claimed is:

1. A cultivated *Capsicum annuum* plant comprising in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 95% amino acid sequence identity to SEQ ID NO: 1, and wherein the mutant allele results in reduced expression or no expression of the wild type SSPER-1 gene and/or wherein the mutant allele encodes a protein having a decreased function or loss-of-function when compared to the wild type protein, wherein the mutant allele encodes a protein that is truncated when compared to the wild type protein and the truncated protein comprises at most amino acids 1-500 of SEQ ID NO: 1.

2. The plant according to claim 1, wherein the truncated protein comprises at most amino acids 1-400 of SEQ ID NO: 1.

3. The plant according to claim 1, wherein the plant is homozygous for the mutant allele.

4. The plant according to claim 1, wherein the plant is an inbred plant, a dihaploid plant or a hybrid plant.

5. A seed from which a plant according to claim 1 can be grown.

6. A plant grown from the seed of claim 5, wherein said plant comprises in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 95% amino acid sequence identity to SEQ ID NO: 1, wherein the mutant allele encodes a protein that is truncated when compared to the wild type protein and the truncated protein comprises at most amino acids 1-500 of SEQ ID NO: 1.

7. A fruit produced by the plant according to claim 1, optionally wherein said fruit is homozygous for the mutant allele of the SSPER-1 gene and is seedless, wherein said fruit comprises in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 95% amino acid sequence identity to SEQ ID NO: 1, wherein the mutant allele encodes a protein that is truncated when compared to the wild type protein and the truncated protein comprises at most amino acids 1-500 of SEQ ID NO: 1.

8. The fruit according to claim 7, wherein the fruit homozygous for the mutant allele of the SSPER-1 gene has the same shape and/or size when compared to the fruits of genetically identical plants comprising two copies of a wild type allele of the SSPER-1 gene.

9. A part of the plant according to claim 1, wherein said plant part is a leaf, anther, pistil, stem, petiole, root, ovule, pollen, protoplast, tissue, seed, flower, cotyledon, hypocotyl, embryo or cell, wherein said part comprises in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 95% amino acid sequence identity to SEQ ID NO: 1, wherein the mutant allele encodes a protein that is truncated when compared to the wild type protein and the truncated protein comprises at most amino acids 1-500 of SEQ ID NO: 1.

10. A vegetatively propagated plant propagated from a plant part according to claim 9.

11. A method of producing stenospermocarpic fruit, said method comprising growing a plant according to claim 1, and harvesting the fruits produced by said plants.

12. A method of identifying and/or selecting a cultivated *Capsicum annuum* plant or plant part comprising a mutant allele of the SSPER-1 gene comprising determining whether the plant or plant part comprises a mutant allele of an SSPER-1 gene, wherein said mutant allele results in reduced expression or no expression of the SSPER-1 gene or wherein the mutant allele encodes a protein having a decreased function or loss-of function when compared to the wild type protein and optionally selecting a plant or plant part comprising at least one copy of a mutant allele of the SSPER-1 gene wherein said mutant allele causes stenospermocarpic fruit formation when present in homozygous form, wherein the wild type SSPER-1 gene encodes a protein comprising at least 95% amino acid sequence identity to SEQ ID NO: 1, wherein the mutant allele encodes a protein that is truncated when compared to the wild type protein and the truncated protein comprises at most amino acids 1-500 of SEQ ID NO: 1.

13. The method according to claim 12, wherein the plant or plant part is subjected to a mutation inducing step prior to determining whether the plant or plant part comprises a mutant allele of an SSPER-1 gene.

14. A method of producing a *Capsicum annuum* plant comprising in its genome at least one copy of a mutant allele of the SSPER-1 gene, wherein said mutant allele causes stenospermocarpic fruit formation when present in homozygous form, said method comprising the step (s) of:

(i) crossing a first *Capsicum annuum* plant and a second *Capsicum annuum* plant, wherein the first *Capsicum annuum* plant is the plant according to claim 1;

(ii) optionally harvesting seed from the crossing of (i) and selecting seed comprising in its genome at least one copy of a mutant allele of the SSPER-1 gene as defined in claim 1.

15. The method of claim 14, wherein in step (i) both the first *Capsicum annuum* plant and the second *Capsicum annuum* plant are plants according to claim 1.

16. A seed obtained from the method of claim 14, wherein said part comprises in its genome at least one copy of a mutant allele of the wild type SSPER-1 gene, wherein said mutant allele causes stenospermocarpic fruit formation when present in homozygous form, wherein the wild type SSPER-1 gene encodes a protein comprising at least 95% amino acid sequence identity to SEQ ID NO: 1, wherein the mutant allele encodes a protein that is truncated when compared to the wild type protein and the truncated protein comprises at most amino acids 1-500 of SEQ ID NO: 1.

17. A plant grown from the seeds of claim 16.

18. A method for the production of a *Capsicum annuum* plant capable of stenospermocarpic fruit formation by growing a seed of claim 5, wherein said plant is homozygous for the mutant allele.

19. The plant according to claim 1, wherein the truncated protein comprises at most amino acids 1-200 of SEQ ID NO: 1.

20. The plant according to claim 1, wherein the mutant allele is SEQ ID NO: 4.

21. The plant according to claim 1, wherein the mutant allele encodes the protein of SEQ ID NO: 3.

* * * * *